United States Patent [19]
Malspeis et al.

[11] Patent Number: 5,824,674
[45] Date of Patent: Oct. 20, 1998

[54] BREFELDIN A DERIVATIVES AND THEIR UTILITY IN THE TREATMENT OF CANCER

[75] Inventors: Louis Malspeis, Frederick; B. Rao Vishnuvajjala, Rockville; Jeffrey G. Supko, Monrovia, all of Md.; Charles Theodore Kane, Jr., Amherst, N.Y.

[73] Assignees: The United States of America as represented by the Department of Health and Human Services, Washington, D.C.; Starks Associates, Buffalo, N.Y.

[21] Appl. No.: 974,902

[22] Filed: Nov. 20, 1997

Related U.S. Application Data

[62] Division of Ser. No. 267,525, Jun. 29, 1994, Pat. No. 5,696,154.

[51] Int. Cl.⁶ .......................... A61K 31/365; A61K 31/55
[52] U.S. Cl. .......................... 514/211; 514/212; 514/218; 514/222.5; 514/228.2; 514/229.2; 514/233.5; 514/241; 514/247; 514/255; 514/359; 514/364; 514/369; 514/372; 514/374; 514/378; 514/383; 514/397; 514/406; 514/450
[58] Field of Search ...................................... 514/450, 211

[56] References Cited

FOREIGN PATENT DOCUMENTS

| | | |
|---|---|---|
| 3247379 | 6/1984 | Germany . |
| 4305249 | 8/1994 | Germany . |
| WO 9521614 | 8/1995 | WIPO . |

OTHER PUBLICATIONS

Haerri, E. et al., *Chemical Abstract* 59, 5726h (1963).

Banerjee, P.K. et al., *Design of Prodrugs*, Bundgaard, H. ed. (Elsevier Science, Amsterdam), pp. 93–96 (1985).

Kovach, I.M. et al., *J. Pharm. Sci.* 64:1070–1071 (1975).

Connors, T.A., *Xenobiotica* 16:975–988 (1986).

*Primary Examiner*—Richard L. Raymond
*Attorney, Agent, or Firm*—Townsend and Townsend and Crew LLP

[57] ABSTRACT

Provided are brefeldin A derivatives of the formula:

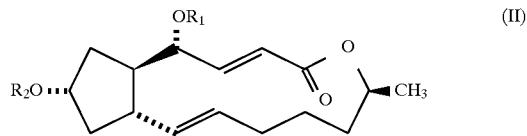

wherein one of $R_1$ and $R_2$ is H and the other of $R_1$ and $R_2$ is a substituent group having 1 to 12 carbon atoms containing a basic nitrogen atom or a quaternary ammonium group, or a salt thereof. These derivatives exhibit good antitumor activity, and are administrable to human patients without the problems associated with brefeldin A.

2 Claims, 27 Drawing Sheets

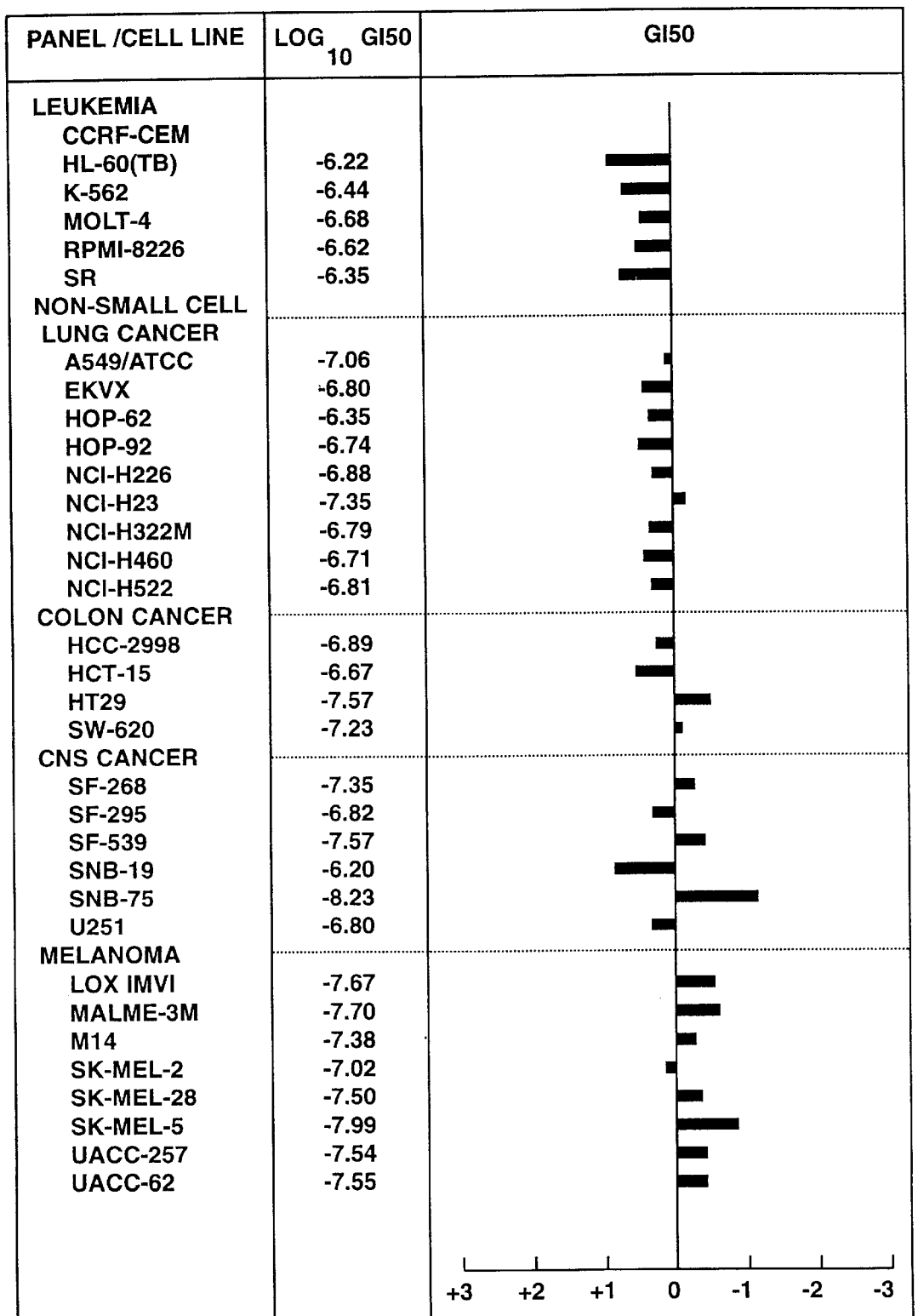
FIG. 1A(1)

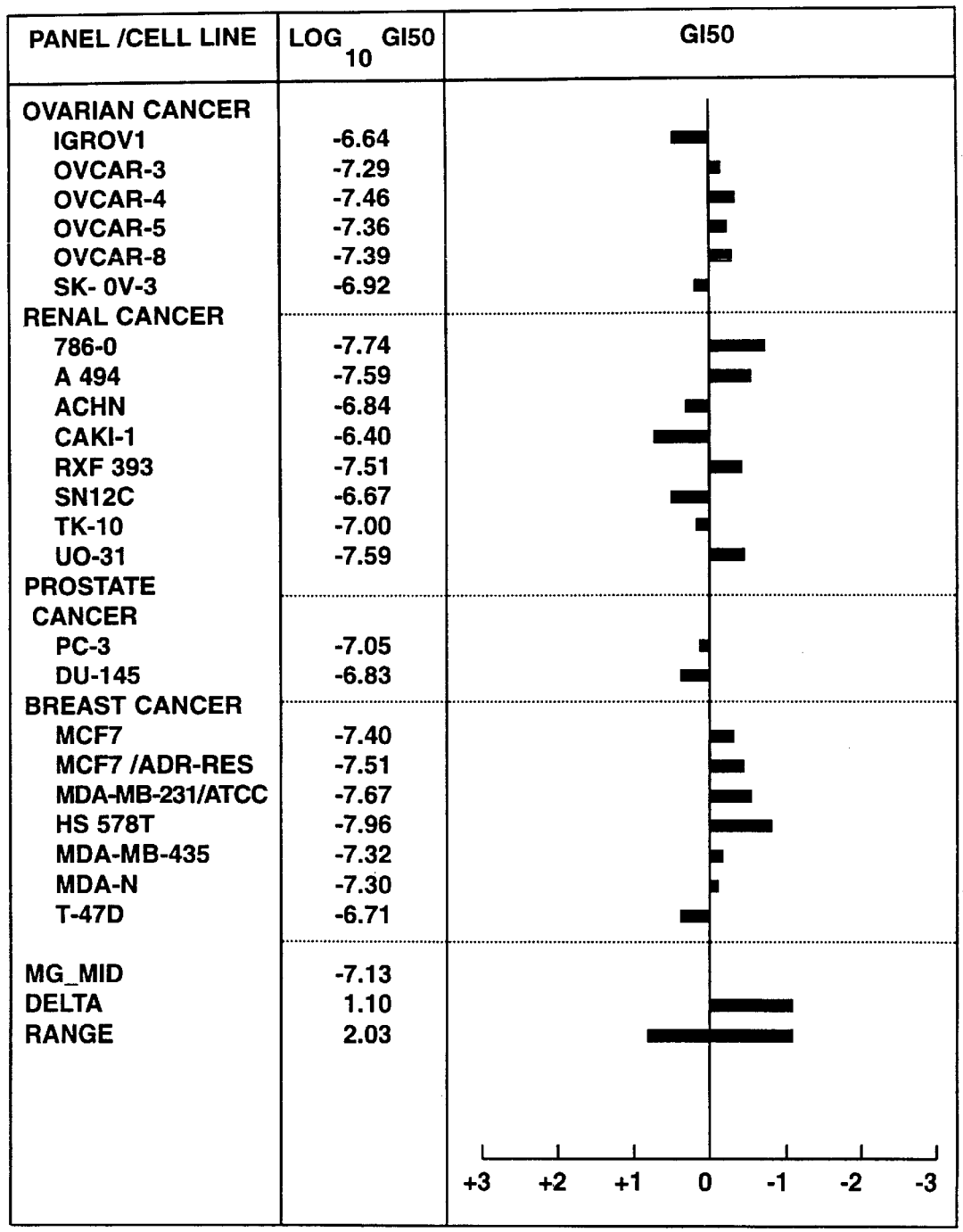
FIG. 1A(2)

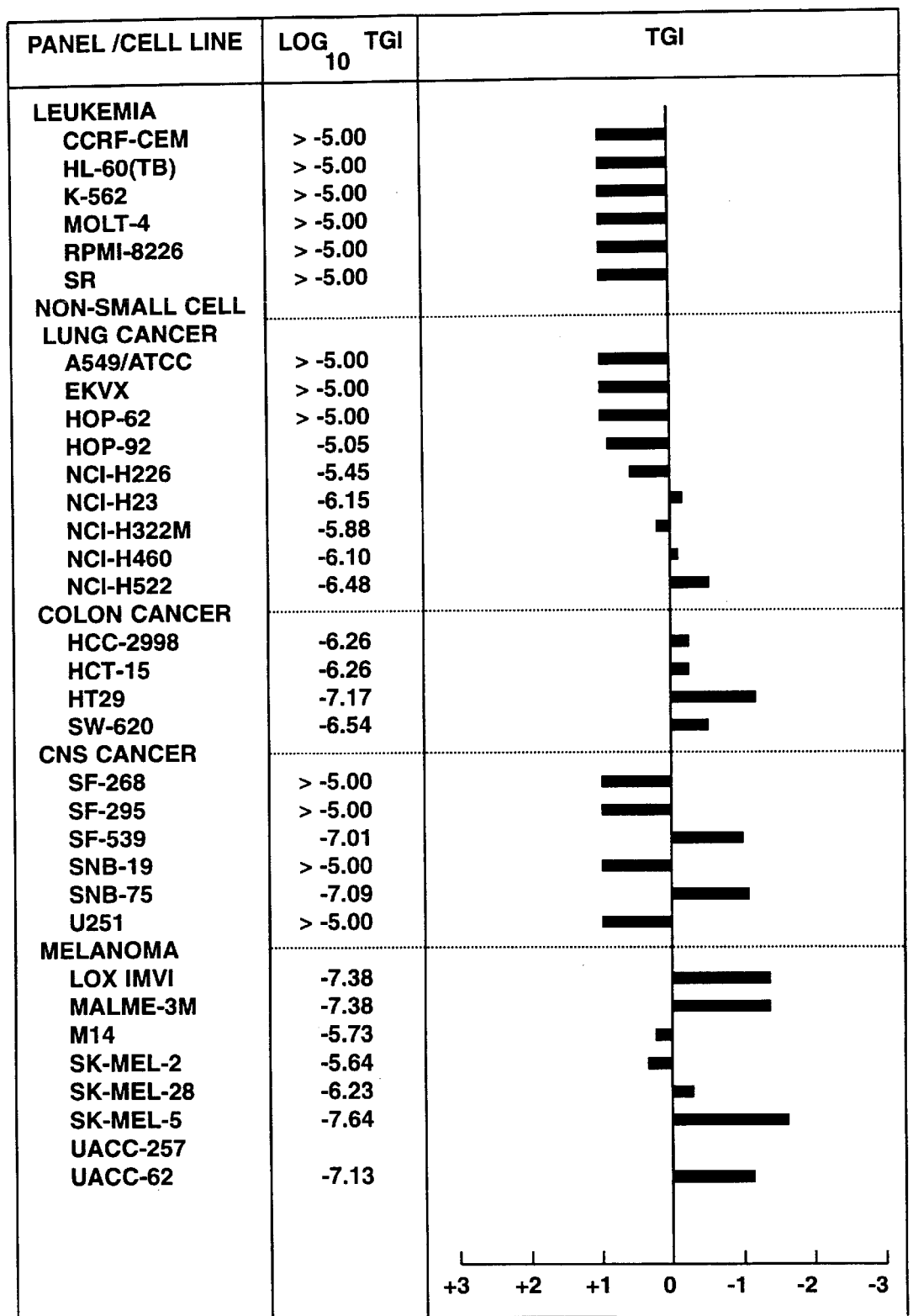
FIG. 1B(1)

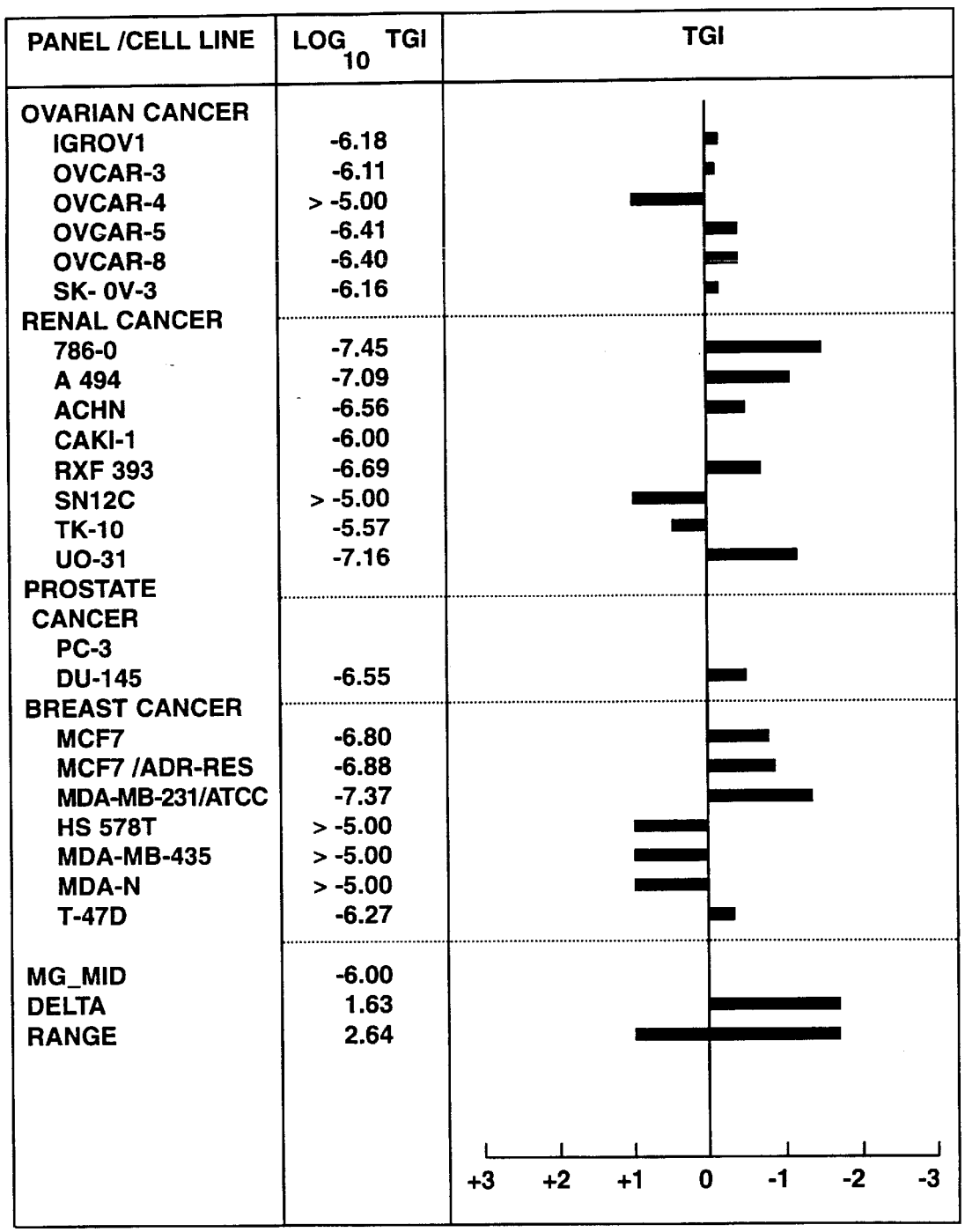
FIG. 1B(2)

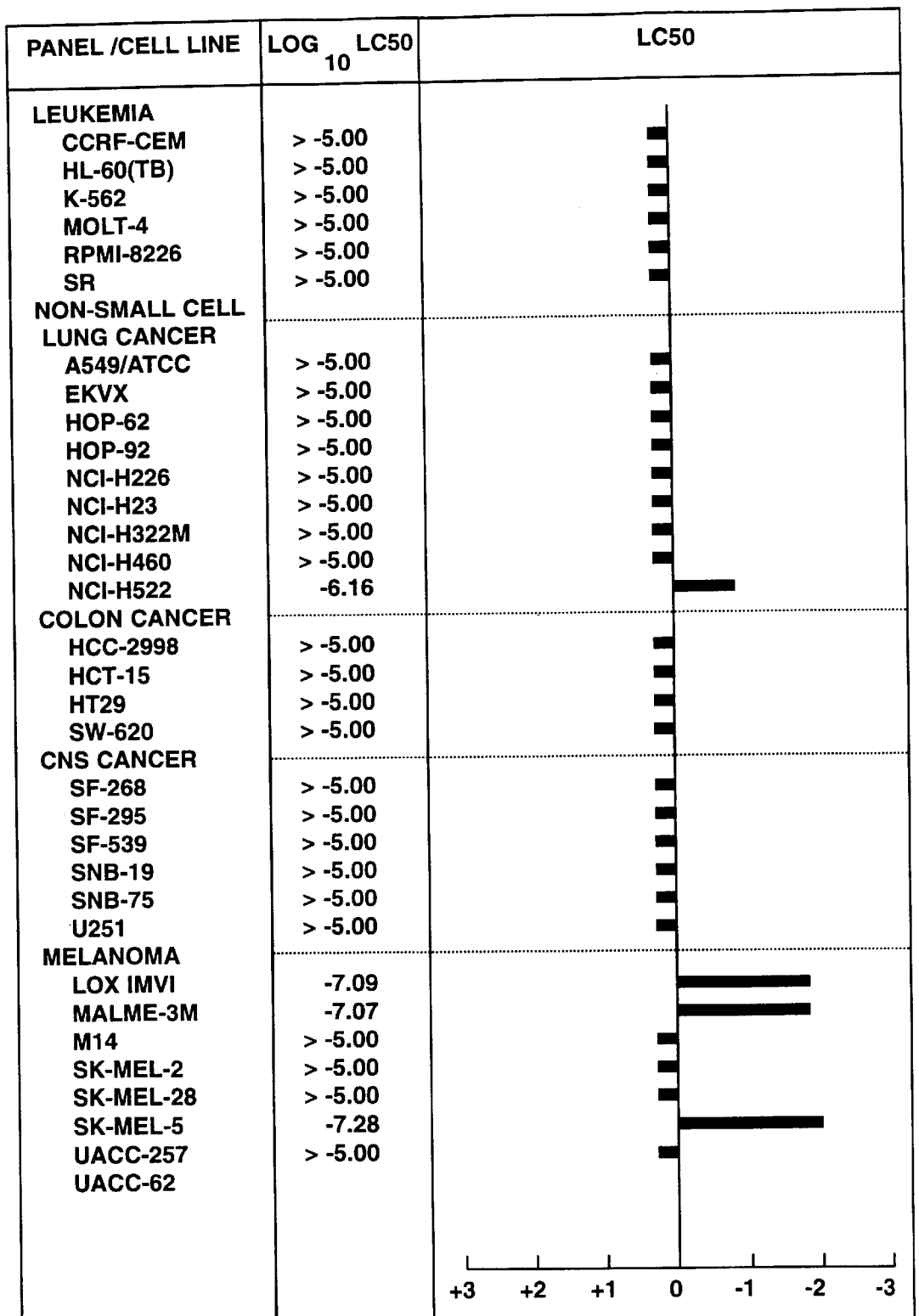
FIG. 1C(1)

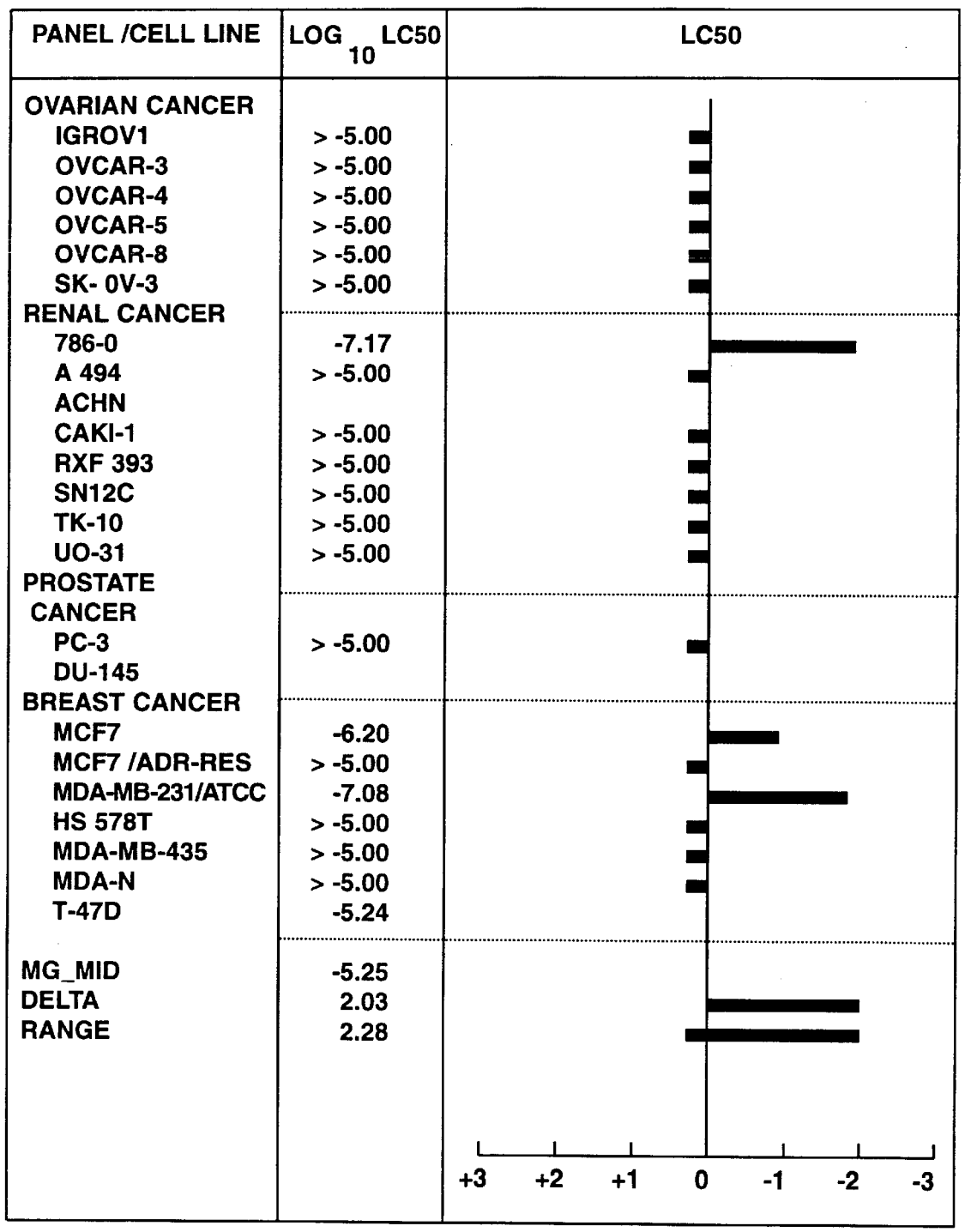
FIG. 1C(2)

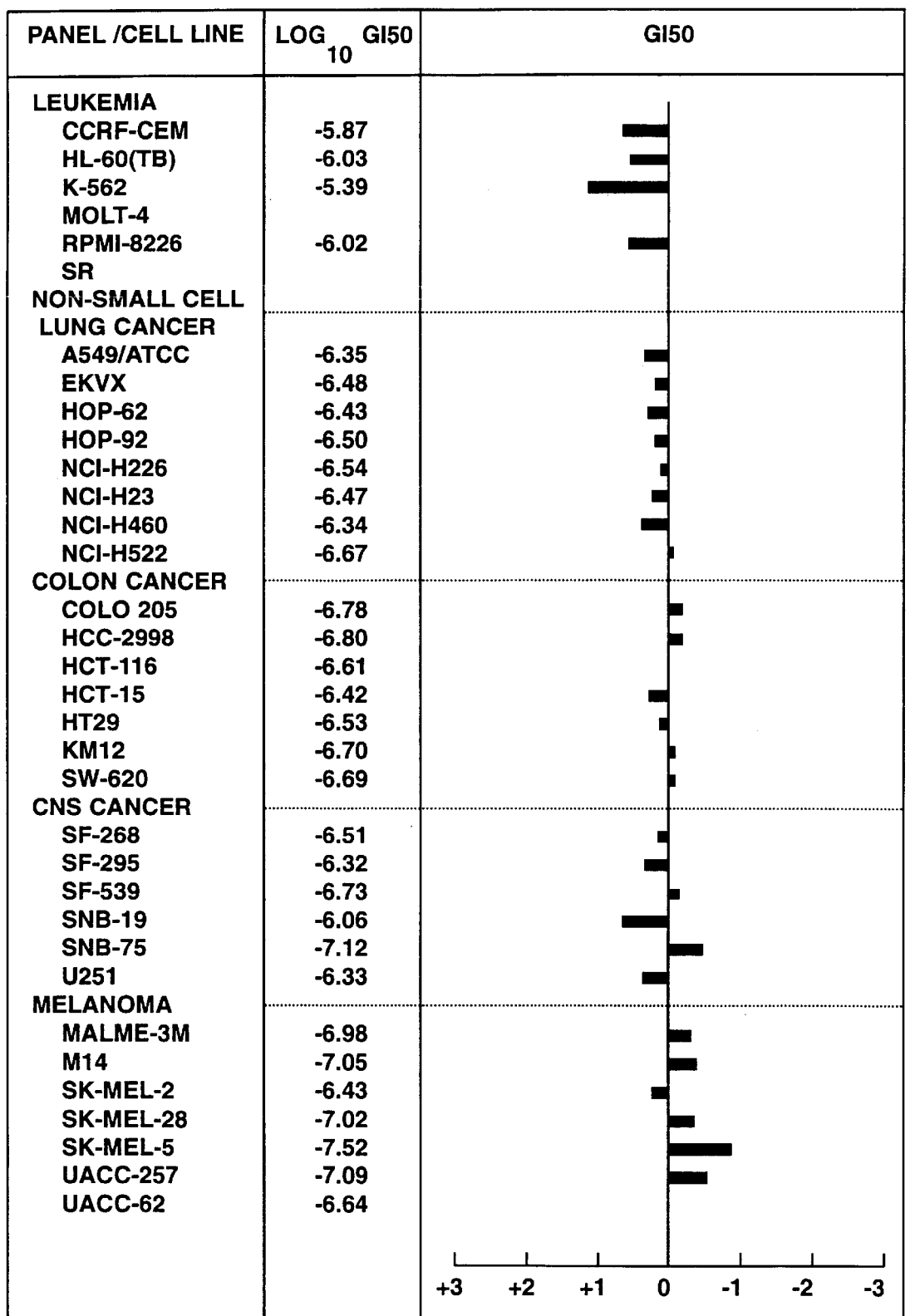
| PANEL /CELL LINE | LOG$_{10}$ GI50 | GI50 |
|---|---|---|
| LEUKEMIA | | |
| CCRF-CEM | -5.87 | |
| HL-60(TB) | -6.03 | |
| K-562 | -5.39 | |
| MOLT-4 | | |
| RPMI-8226 | -6.02 | |
| SR | | |
| NON-SMALL CELL LUNG CANCER | | |
| A549/ATCC | -6.35 | |
| EKVX | -6.48 | |
| HOP-62 | -6.43 | |
| HOP-92 | -6.50 | |
| NCI-H226 | -6.54 | |
| NCI-H23 | -6.47 | |
| NCI-H460 | -6.34 | |
| NCI-H522 | -6.67 | |
| COLON CANCER | | |
| COLO 205 | -6.78 | |
| HCC-2998 | -6.80 | |
| HCT-116 | -6.61 | |
| HCT-15 | -6.42 | |
| HT29 | -6.53 | |
| KM12 | -6.70 | |
| SW-620 | -6.69 | |
| CNS CANCER | | |
| SF-268 | -6.51 | |
| SF-295 | -6.32 | |
| SF-539 | -6.73 | |
| SNB-19 | -6.06 | |
| SNB-75 | -7.12 | |
| U251 | -6.33 | |
| MELANOMA | | |
| MALME-3M | -6.98 | |
| M14 | -7.05 | |
| SK-MEL-2 | -6.43 | |
| SK-MEL-28 | -7.02 | |
| SK-MEL-5 | -7.52 | |
| UACC-257 | -7.09 | |
| UACC-62 | -6.64 | |
FIG. 2A(1)
| 2A(1) |
|---|
| 2A(2) |

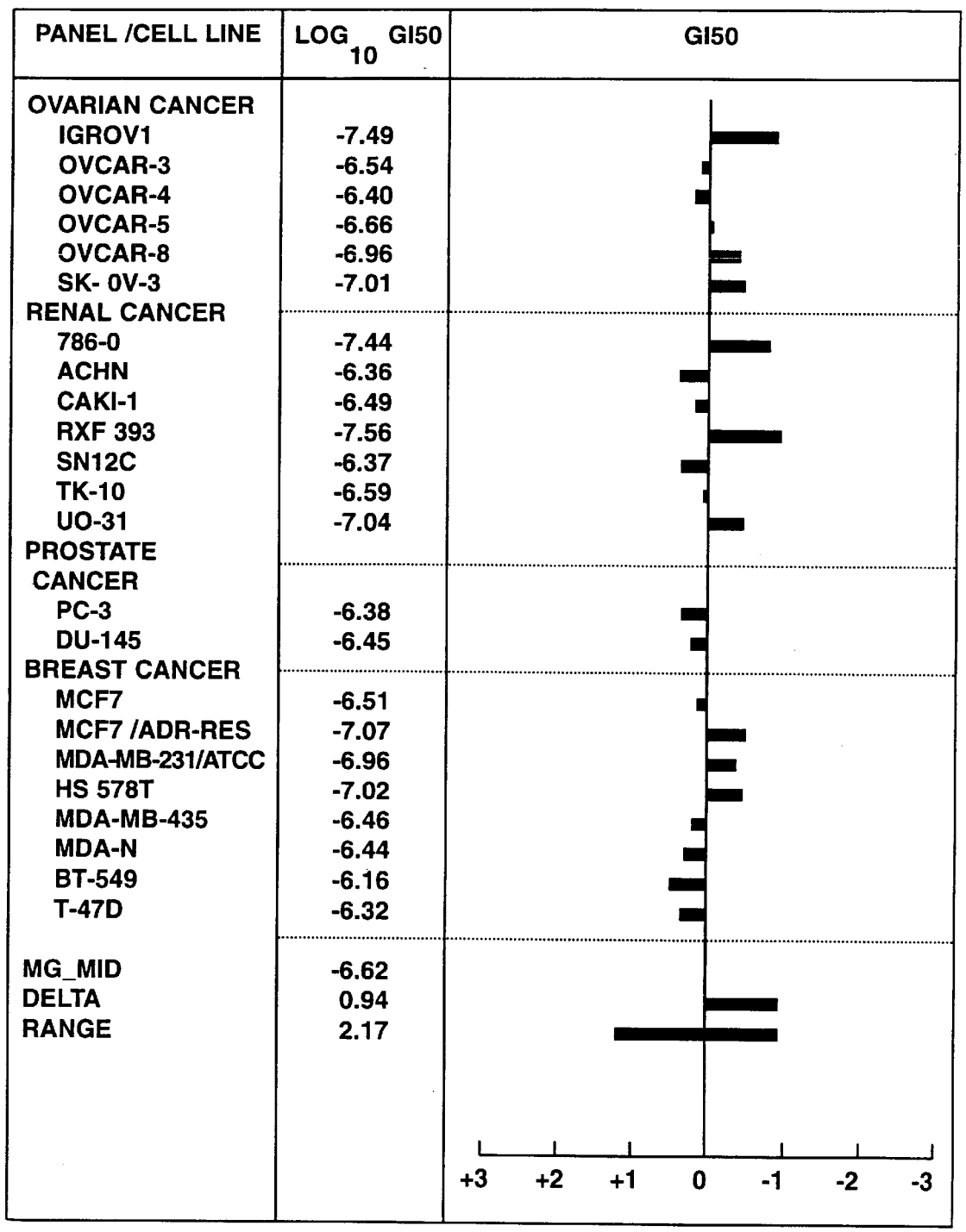
FIG. 2A(2)

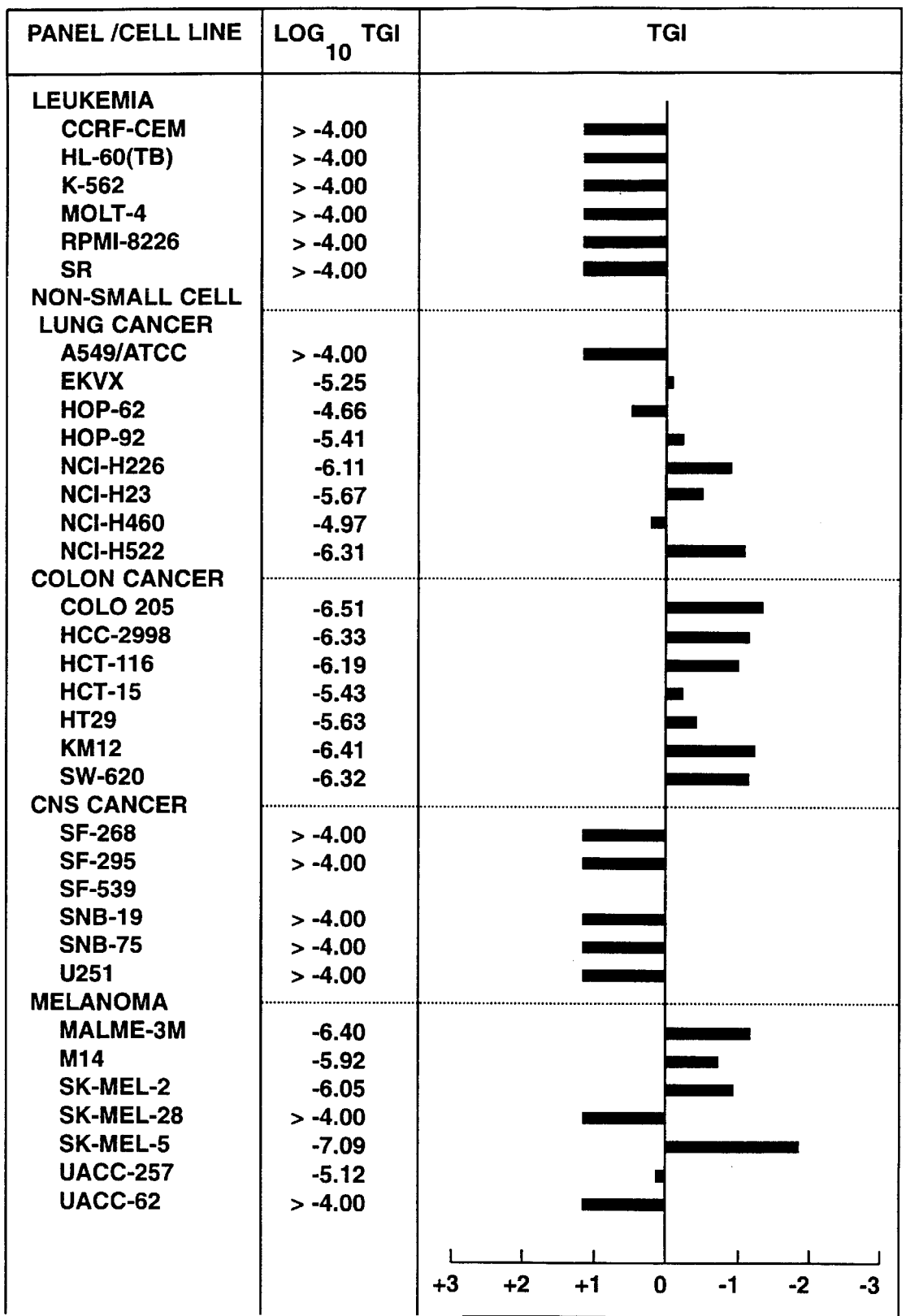
FIG. 2B(1)

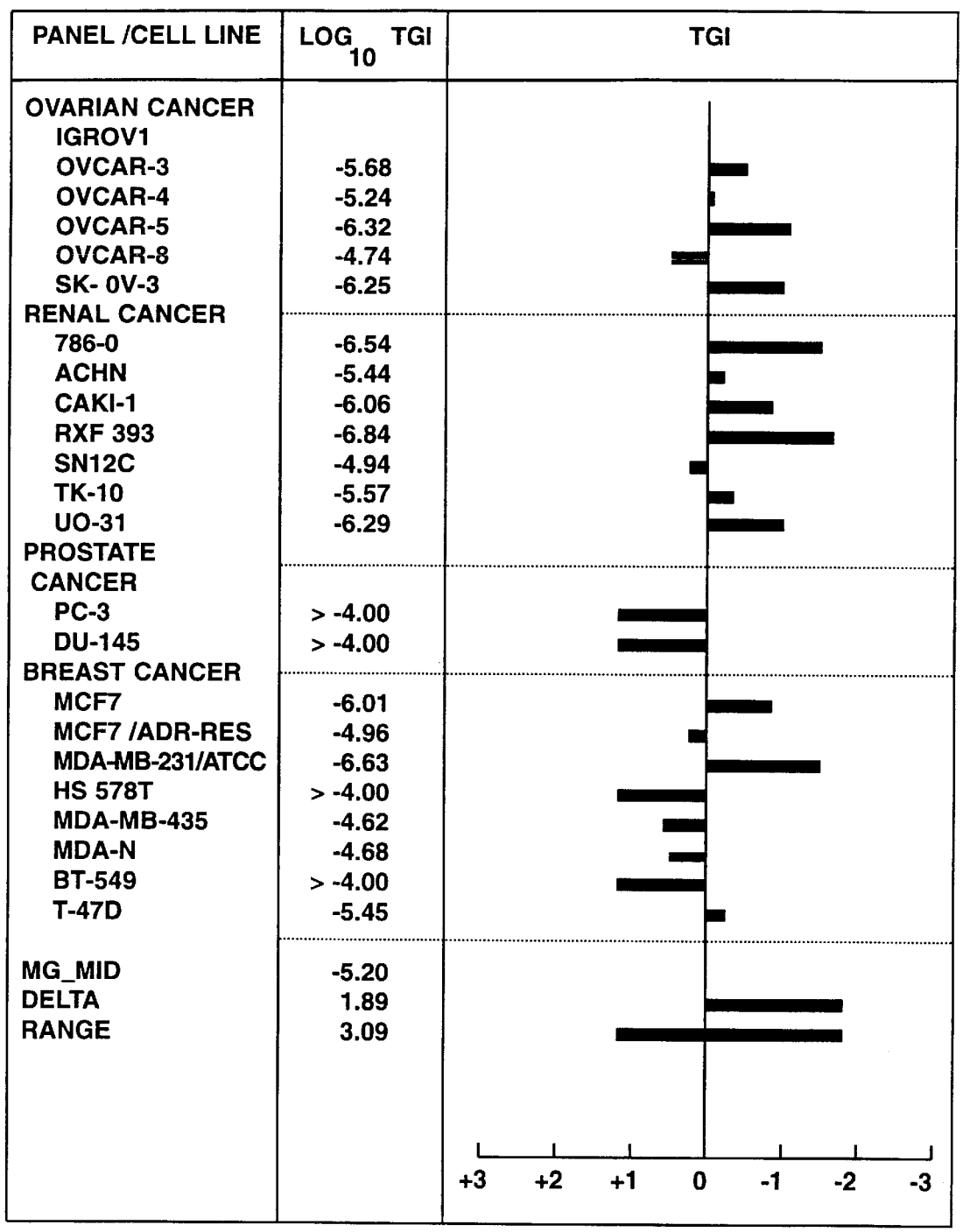
FIG. 2B(2)

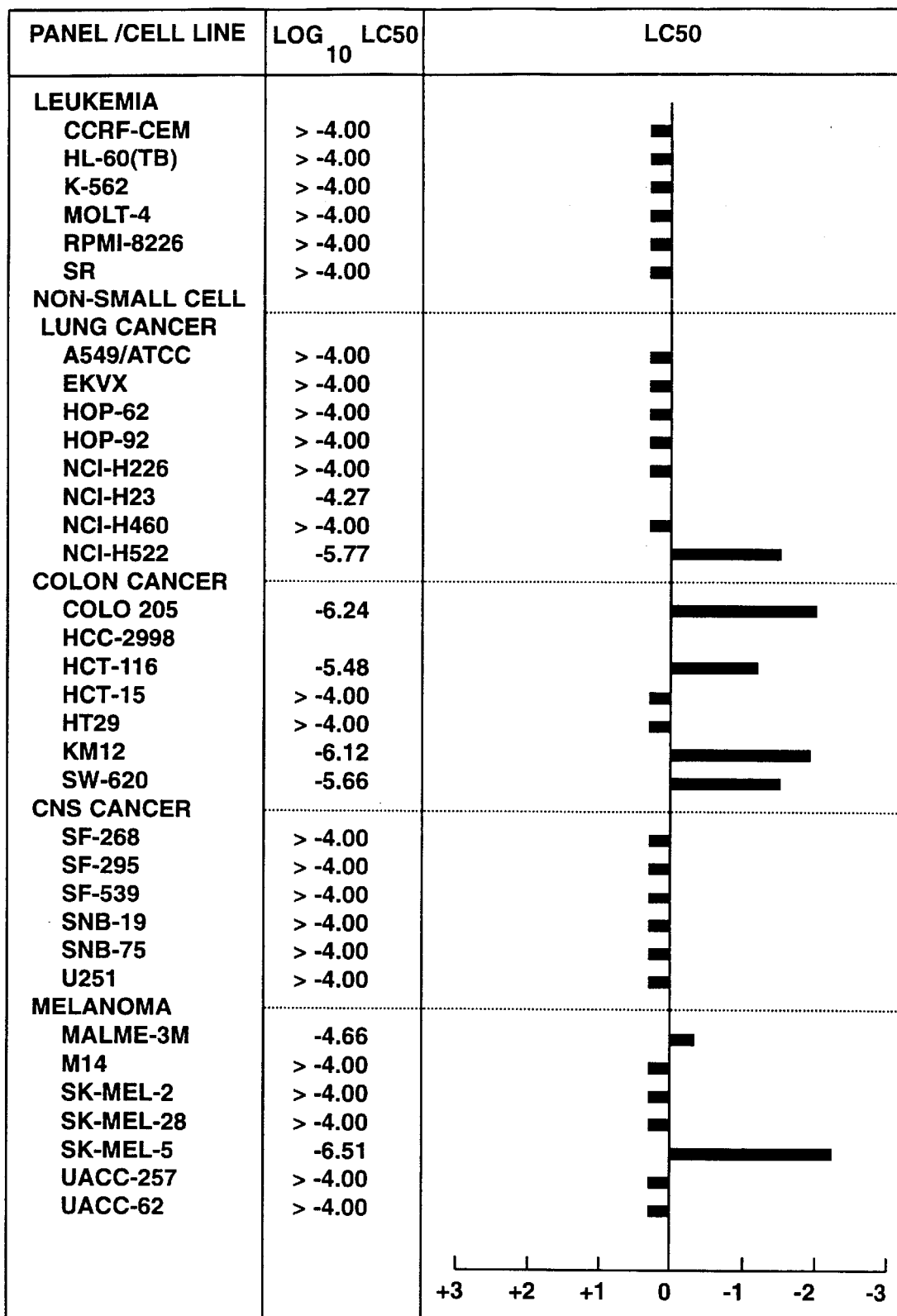
FIG. 2C(1)

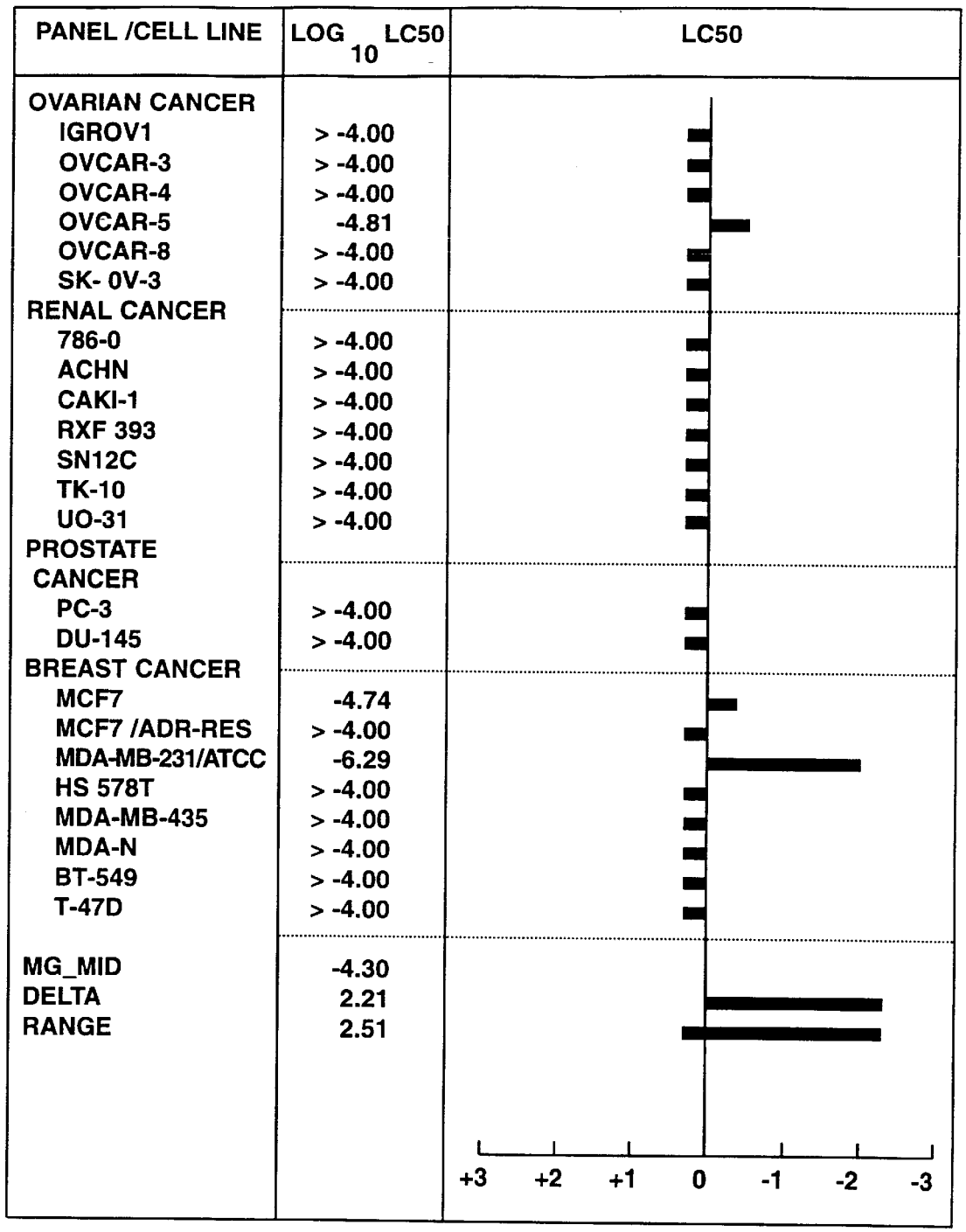
FIG. 2C(2)

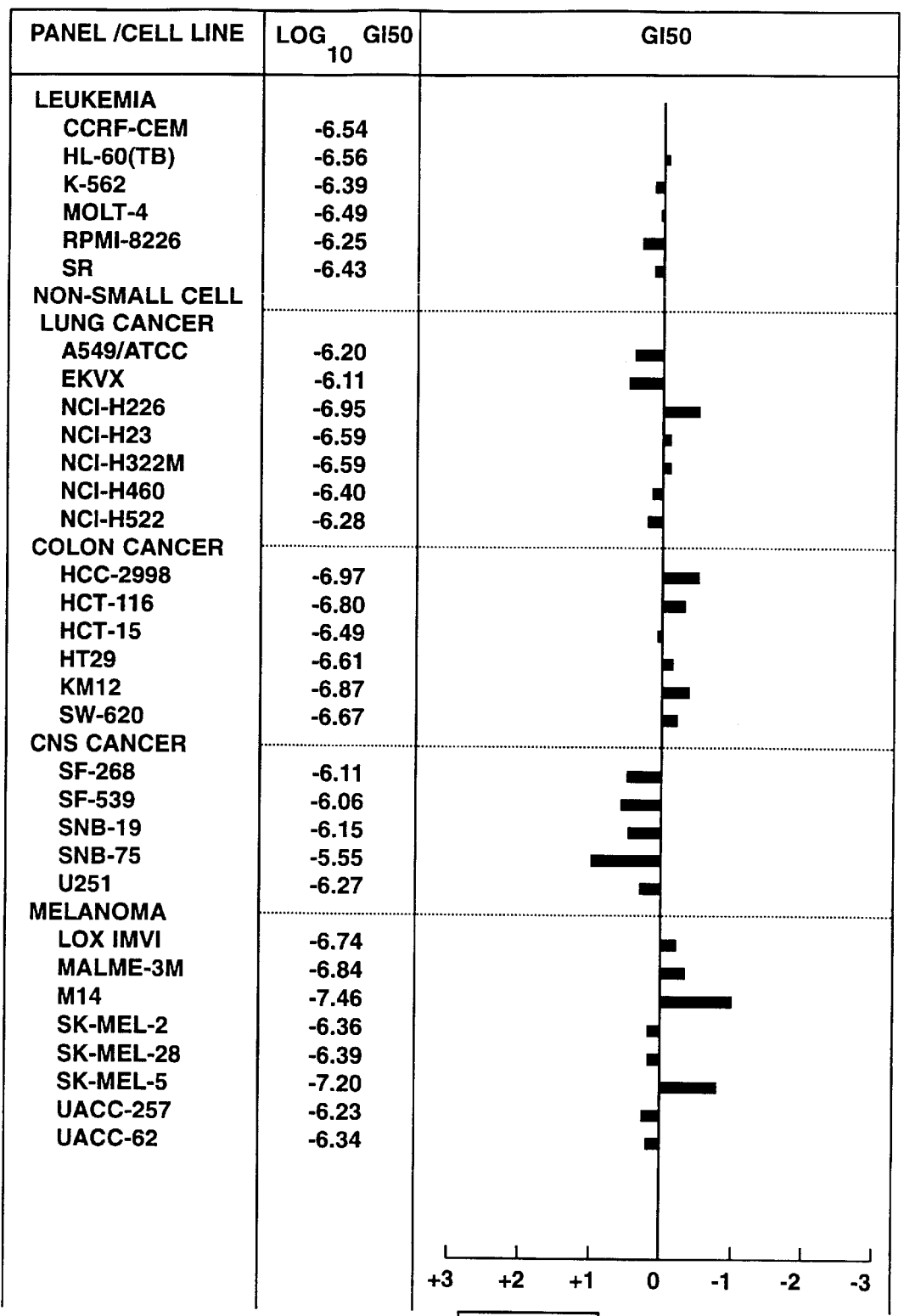
FIG. 3A(1)

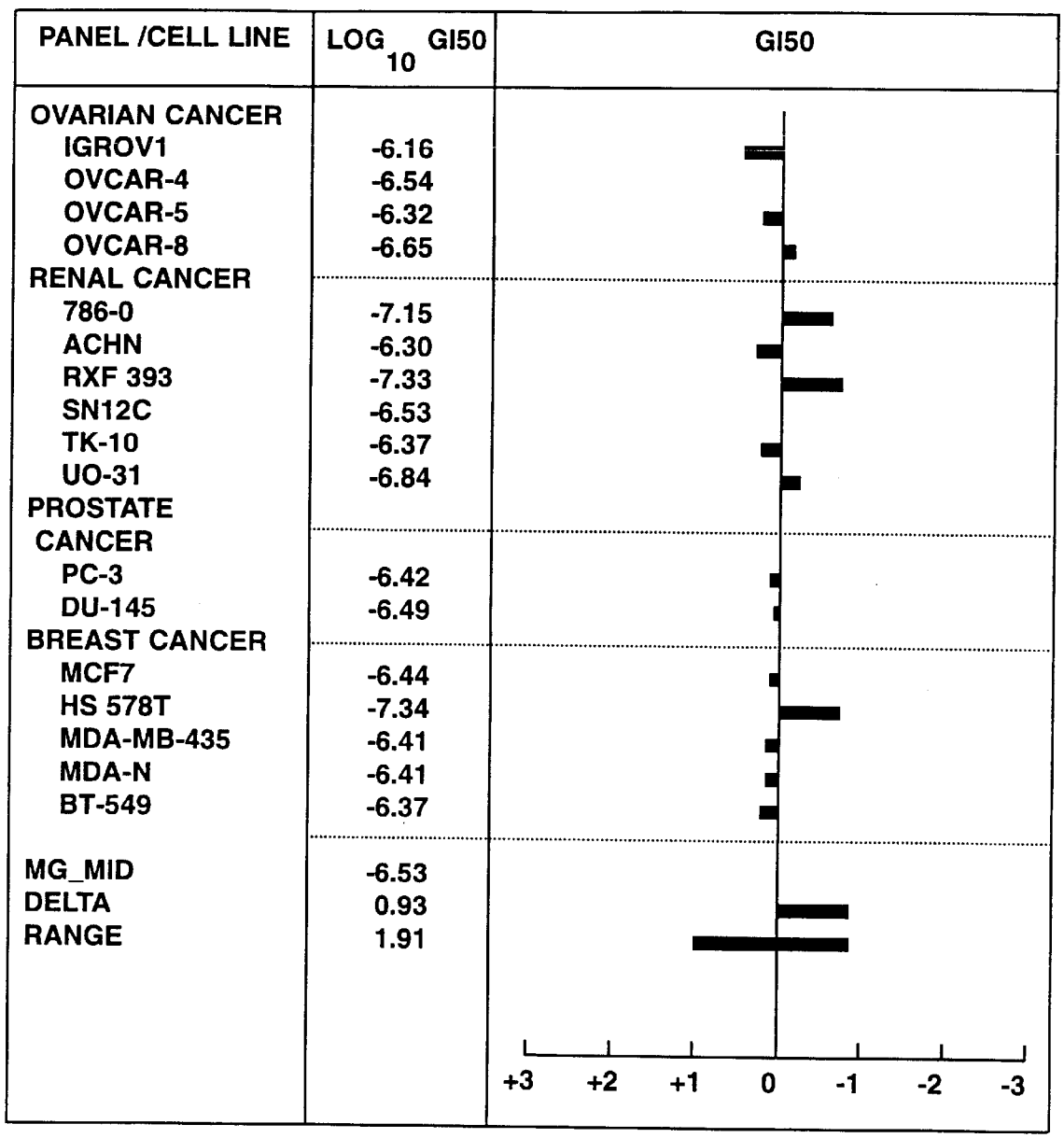
FIG. 3A(2)

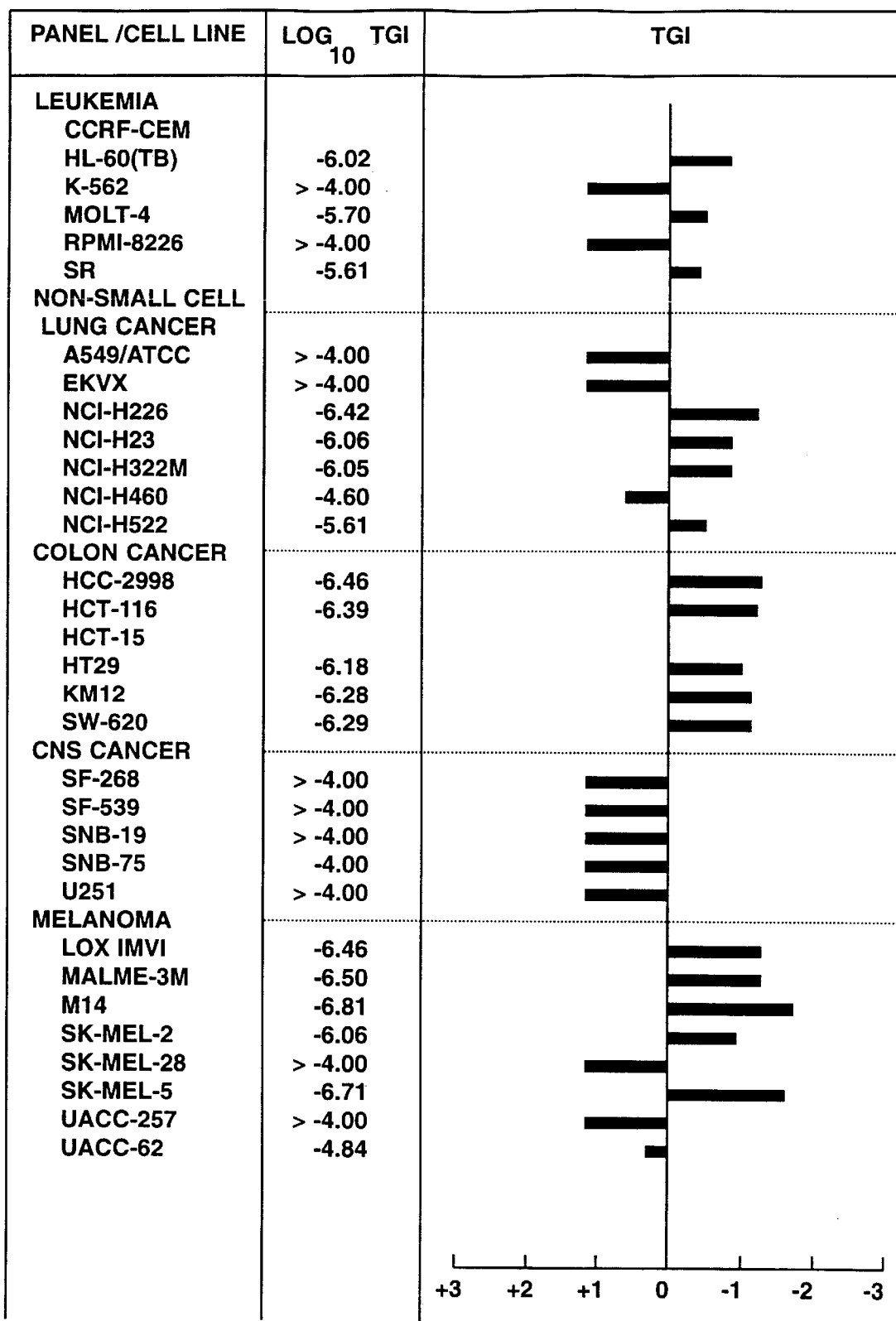
FIG. 3B(1)

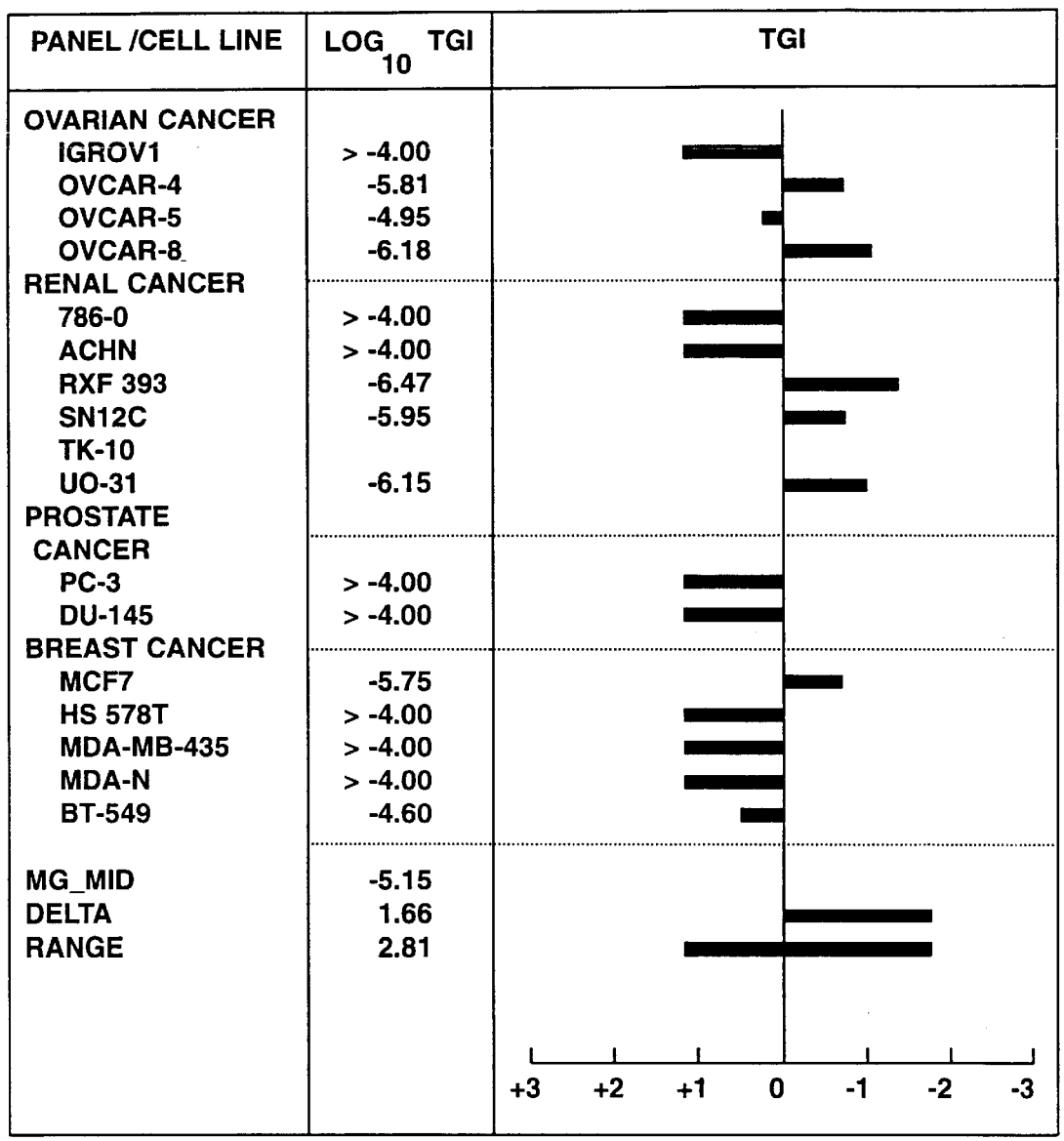
FIG. 3B(2)

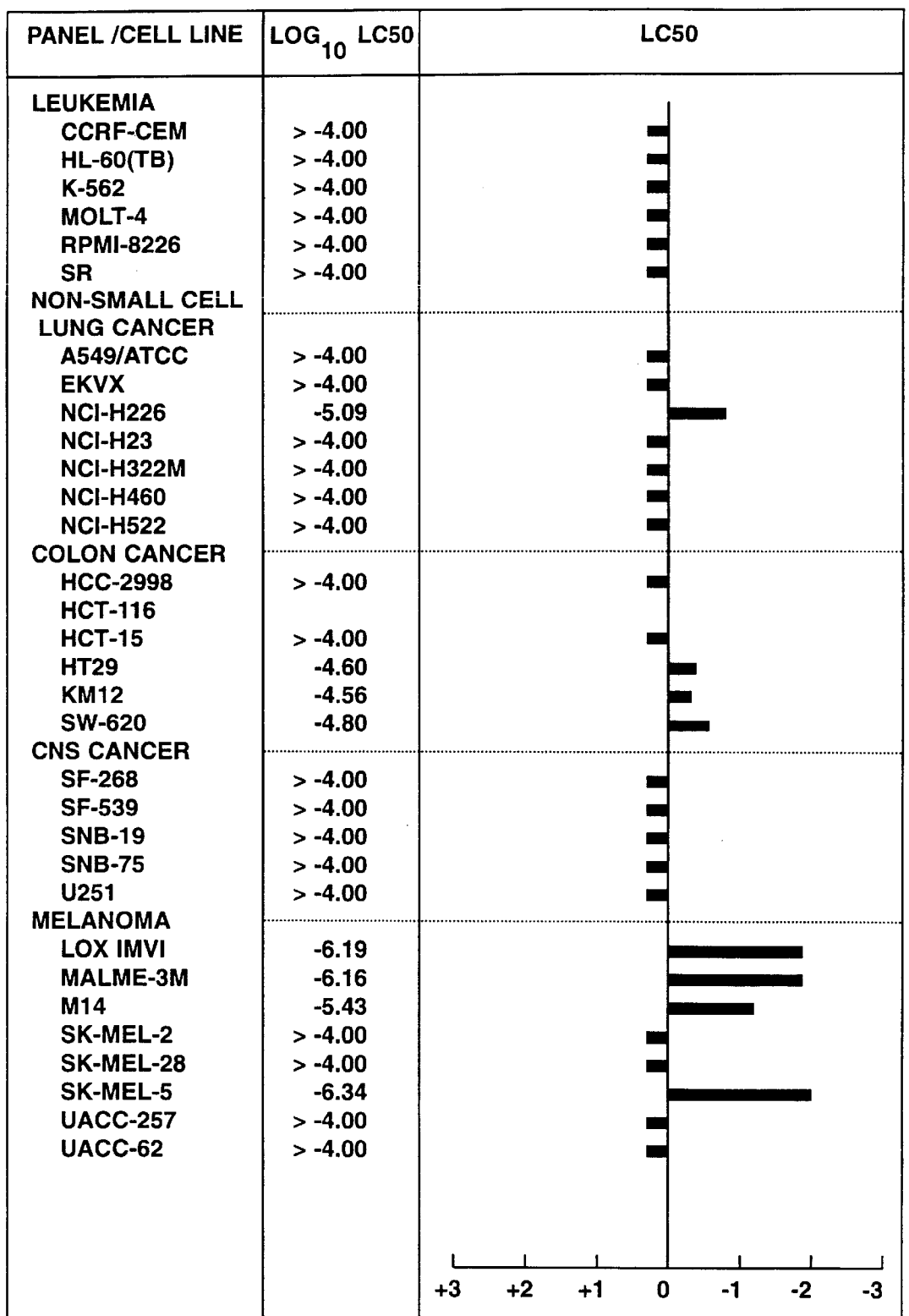
FIG. 3C(1)

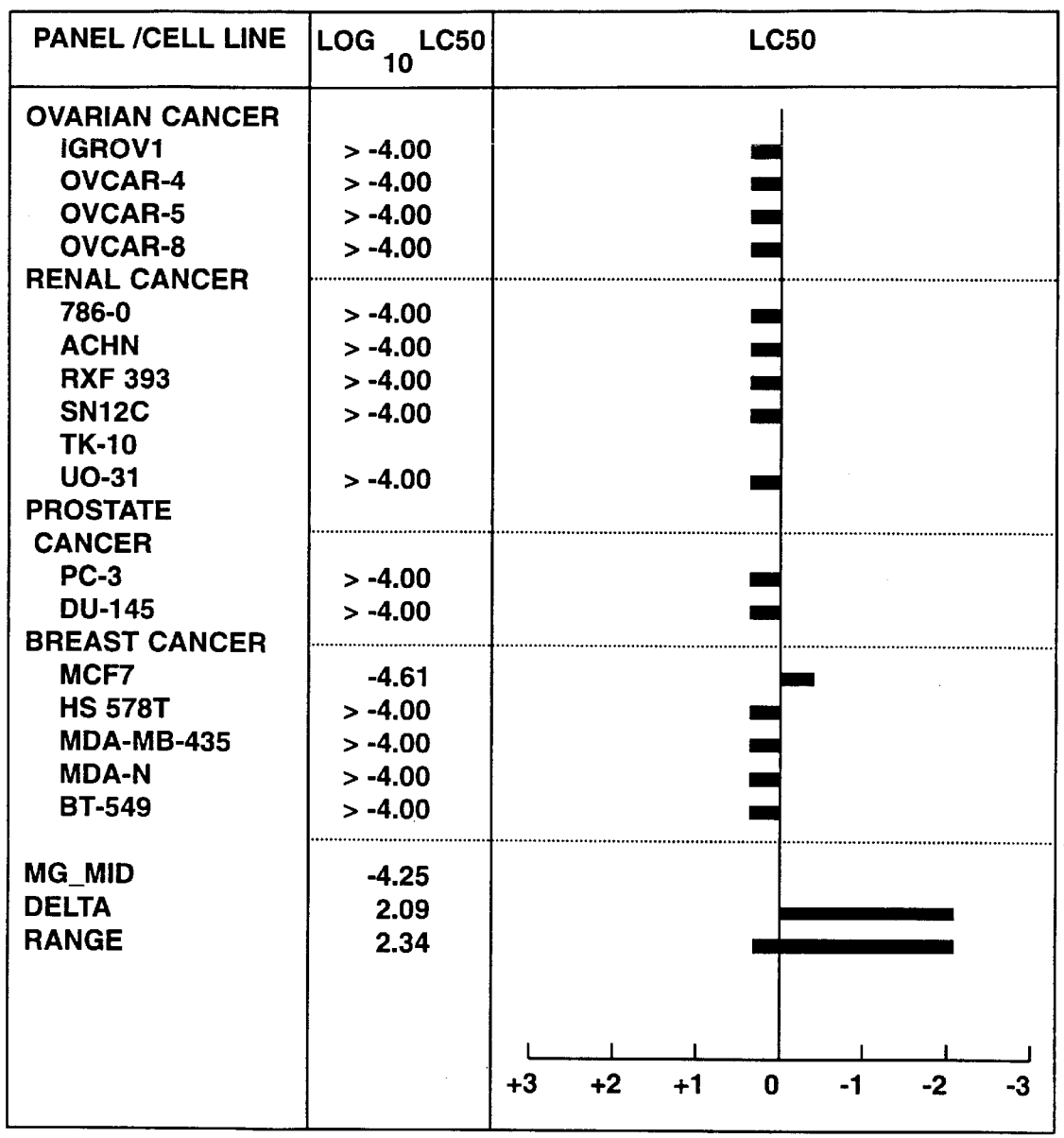
FIG. 3C(2)

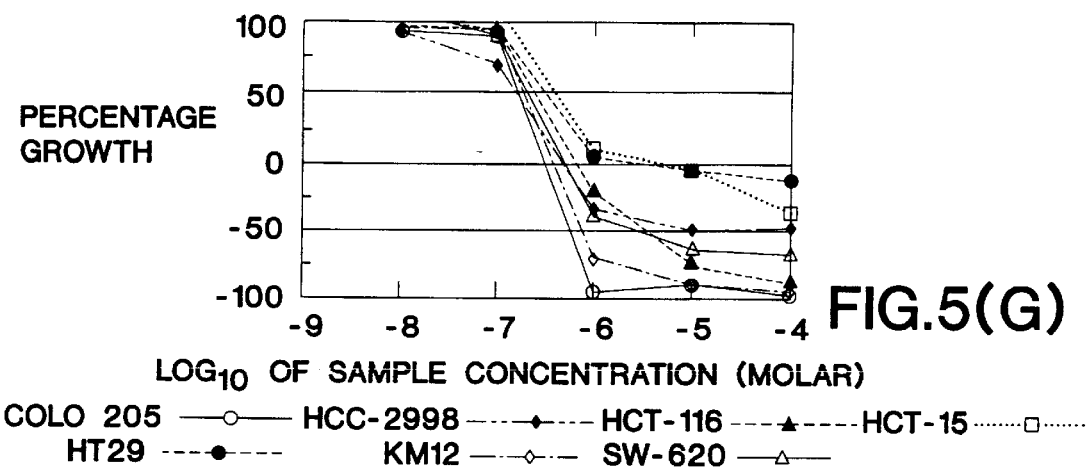
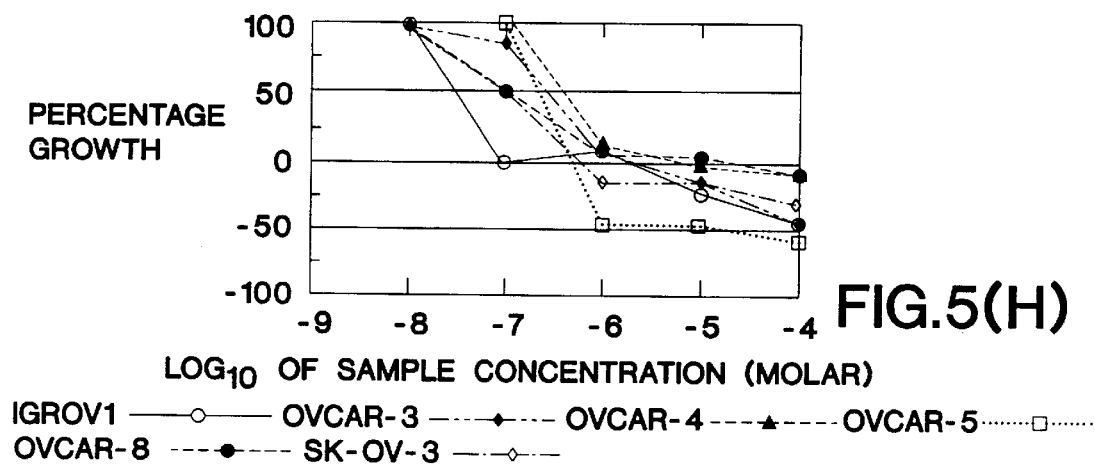
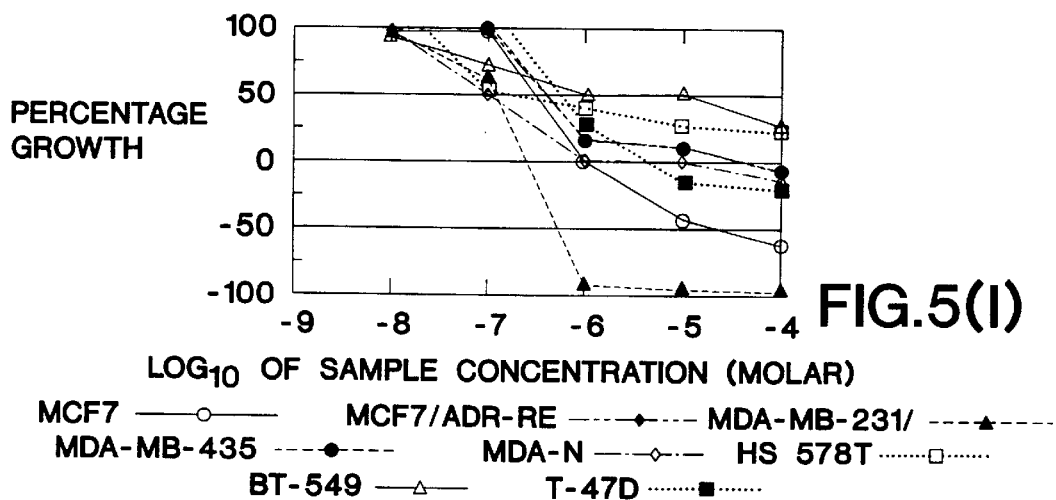

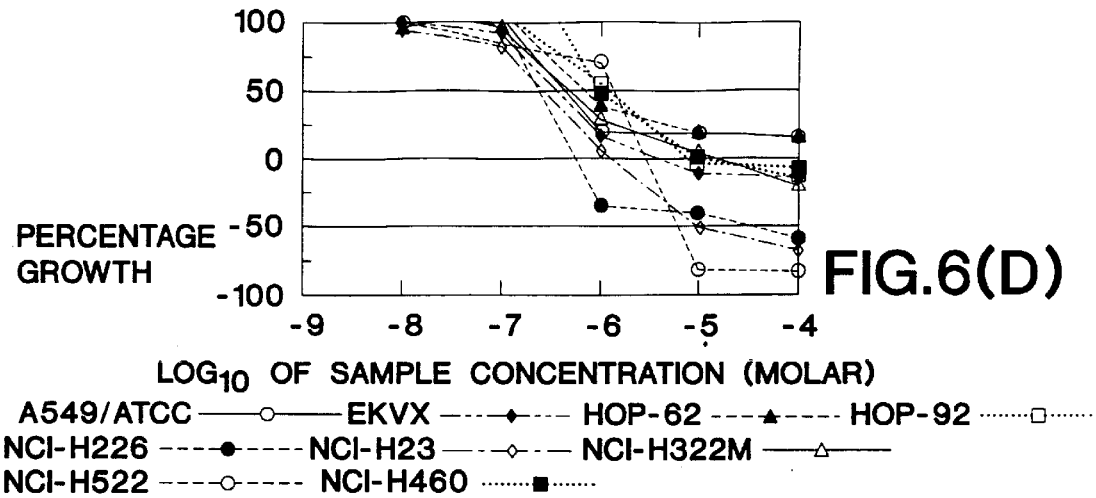
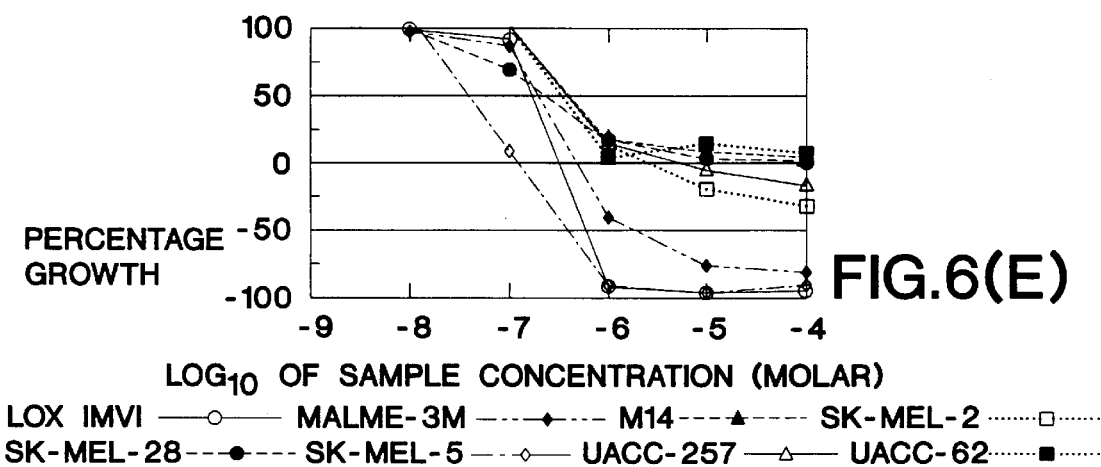
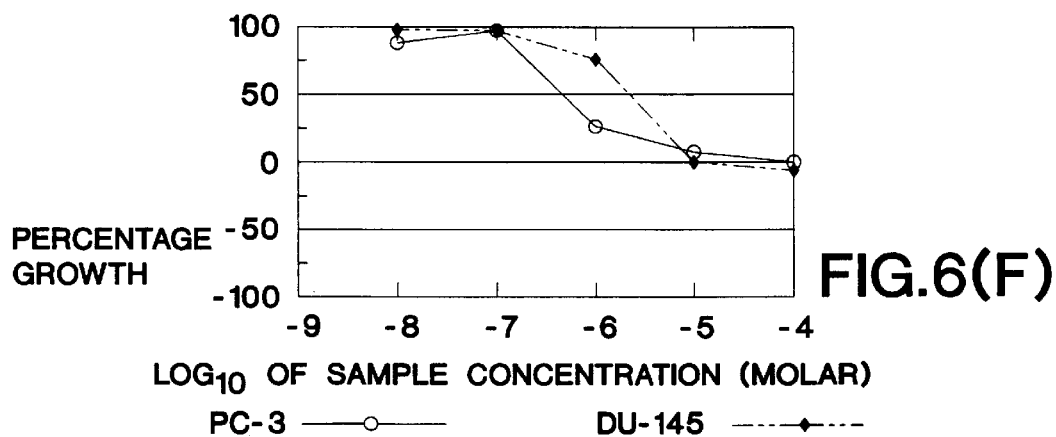

BREFELDIN A DERIVATIVES AND THEIR UTILITY IN THE TREATMENT OF CANCER

This is a Division of application Ser. No. 08/267,525 filed Jun. 29, 1994, now U.S. Pat. No. 5,696,154, the disclosure of which is incorporated by reference.

BACKGROUND OF THE INVENTION

1. Field of the Invention

The present invention relates to new derivatives of brefeldin A, pharmaceutical compositions containing the same, and methods of treating cancer, including colon cancer, melanoma, leukemia, ovarian, prostate, breast, and renal tumors, by administration of these derivatives.

2. Description of Related Art

Brefeldin A has the structure set forth in formula (I) as elucidated by Sigg (1964).

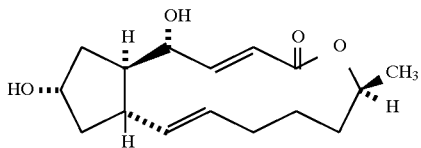

This compound was first described as an antifungal, cytotoxic, and cancerostatic antibiotic (Harri et al. 1963). Additional biological effects were later reported, and Betina summarized the biological activities of brefeldin A (V. Betina, Folia Microbiol., 37, 3–11 (1992)). These activities include: antibiotic, antifungal (Betina et al., Naturweis, 49, 241 (1962); Betina et al., Ann. Ins. Pasteur, 109, 833–842 (1965)); phytotoxic (for example, Suzuki et al., Agric. Biol. Chem., 34, 395–413 (1970)); cytotoxic (Ishii et al., J. Antibiot. 42, 1877–1878 (1989)); and antiviral properties (Tamura et al., J. Antibiot., 21, 160–161 (1968)). Acker et al. (U.S. Pat. No. 4,608,078) describe the preparation of an extensive collection of brefeldin A derivatives and their usefulness as herbicides for controlling undesirable plant growth.

Brefeldin A has been shown to have a profound effect on the structure of the Golgi apparatus within cells, and is believed to interfere with the transport of proteins through the cytoplasm (Lippincott-Schwartz et al., Cell, 56, 801–813 (1989) and J. Cell. Biol., 112, 567–577 (1991); Domes R. W. et al., J. Cell. Biol., 109, 61–72 (1989)).

In 1963, brefeldin A was presented to the National Cancer Institute for development as a possible anti-cancer drug. During the early development, only marginal in vivo activity could be demonstrated in murine tumor models. Further studies demonstrated that this activity was accompanied by unacceptable toxicities due to the vehicles used in these studies, and further development of brefeldin A was discontinued (DIS Minutes: NSC89671, unpublished data from NCI).

Betina et al. (Folia Microbiol. 13, 495–500, 1968) disclosed the preparation of tetrahydro brefeldin A and di-O-acetyl brefeldin A (brefeldin A was described as cyanein, a name used previously by this author) and tested for antifungal properties. However, these compounds possess insufficient solubility to be suitable for intravenous use in humans. Acker et al. (U.S. Pat. No. 4,608,078) disclosed a number of brefeldin A derivatives (analogs) modified by functionalizing both the secondary hydroxyl groups with alkyl, aralkyl, phosphoryl, alkylphosphoryl, alkanoyl, halogen substituted alkanoyl, and silyl derivatives. None of these derivatives, however, is disclosed to be soluble in water or suitable for human therapy. Furthermore, the derivatives described in Acker et al. were claimed to be useful as herbicides after mixing with organic solvents and surfactants, implying lack of adequate water solubility, and potential vehicle related toxicity if given to either experimental animals, human subjects, or patients.

SUMMARY OF THE INVENTION

The present inventors have now overcome this deficiency through synthetic modification of brefeldin A to provide brefeldin A derivatives useful in the treatment of human neoplasms. In addition, they recently discovered that brefeldin A possesses both cytostatic and cytotoxic activity in human tumor cell lines. Further, they discovered that the actions of brefeldin A in these cell lines are both selective and specific when the cell lines were grouped by disease sites such as melanoma, breast, etc. as shown by the bar graphs depicted in FIG. 1. An explanation of Developmental Therapeutics screening program and interpretation of data is provided in Seminars in Oncology, 19 (6), 1992, pp. 622–638. The bar graphs of FIG. 1 clearly demonstrate that human cancer cell lines represented by colon, melanoma, prostate, breast and renal are very sensitive to brefeldin A compared to leukemia, CNS and ovarian cell lines. These results also demonstrated that the total growth inhibition in these sensitive cell lines could be achieved at concentrations as low as 10 nanomoles/L. For selected cell lines (e.g., 786-0 renal and M-19 melanoma), brefeldin A also possesses cytocidal activity at lower concentrations.

This information rekindled interest at NCI in developing brefeldin A for clinical use. However, since previous experience showed that brefeldin A could not be given to animals without unacceptable vehicle toxicity, the present inventors sought to design analogs that retain the cytostatic and cytotoxic effects of the parent compound, and yet are suitable for intravenous delivery to experimental animals and cancer patients.

Accordingly, it is therefore an object of the present invention to overcome the above-noted deficiencies of the prior art. Specifically, the present invention provides new chemical species of brefeldin A produced by structural modification thereof in order to produce chemically stable, nitrogen-containing water-soluble compounds that are compatible with blood and blood products. Thus, these chemical species can be safely administered to patients by intravenous route without the need for potentially toxic organic solvents or surfactants.

In addition to a lactone function, brefeldin A contains two secondary hydroxyl groups. In the present invention, these hydroxyl groups are selectively converted to produce monoesters (Formulas III and IV, below) by separate synthetic methods. The chemical moiety for the esterification was chosen in part from the amino acids, which contain both carboxyl and amine functions. While the carboxyl function is bound in the form of an ester with brefeldin A, the amine function of these derivatives is free to form salts with any of the common acids such as hydrochloric acid, lactic acid, citric acid, etc. It is these salt forms that impart high water solubility to the new compounds of the present invention. While such chemical modifications do not always result in retention of biological activity of the parent drug, evidence presented below demonstrates that the derivatives described herein possess anti-tumor activity similar to brefeldin A.

Accordingly, it is another object of the present invention to provide a compound of the formula:

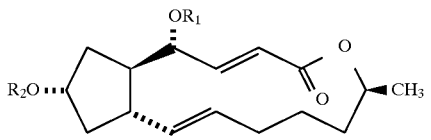

(II)

wherein one of $R_1$ and $R_2$ is H and the other of $R_1$ and $R_2$ is a substituent group having 1 to 12 carbon atoms containing a basic nitrogen atom or a quaternary ammonium group, or a salt thereof.

Another object of the present invention is to provide a pharmaceutical composition comprising an effective antitumor amount of at least one of the foregoing compounds or pharmaceutically acceptable salt thereof, and a pharmaceutically acceptable carrier, diluent, or excipient.

Yet another object of the present invention is to provide a method for treating tumors, which comprises administering to a patient an effective antitumor amount of at least one of the foregoing compounds. Human colon cancer, melanoma, leukemia, ovarian, prostate, breast, and renal tumors can be treated with these compounds.

The compounds of the present invention are also useful intermediates for the preparation of brefeldin A. The compounds of the present invention can be easily stored for long periods of time, with good stability in dried form. Subsequently, the compounds can be dissolved, and then easily converted into the parent compound brefeldin A by reaction with hydrochloric acid or hydrobromic acid.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only and are not limitative of the present invention, in which:

FIGS. 1–3 are bar graphs showing the results of tests with various human tumor cell lines.

DETAILED DESCRIPTION OF THE INVENTION

Figure 4A:
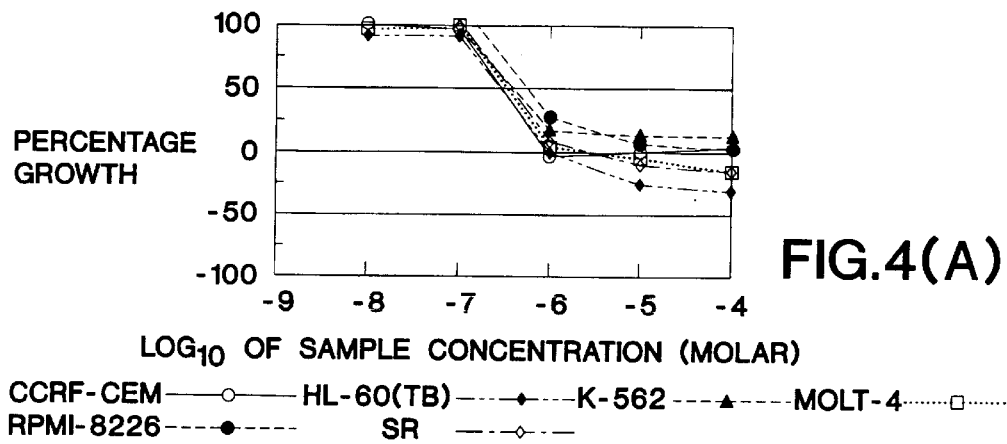
FIGS. 4–6 are dose response curves based on the results of the tests with various human tumor cell lines.

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The brefeldin A derivatives of the present invention are represented by the following formula:

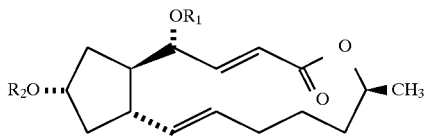

(II)

wherein one of $R_1$ and $R_2$ is H and the other of $R_1$ and $R_2$ is a substituent group having 1 to 12 carbon atoms containing a basic nitrogen atom or a quaternary ammonium group, or a salt thereof. This substituent group can more preferably have 1 to 8 carbon atoms, most preferably 1 to 4 carbon atoms.

Soluble derivatives of brefeldin A suitable for injection can be esters in which the basic nitrogen atom or quaternary ammonium group can be converted to a water-soluble salt by the addition of a suitable acid.

Compounds of the present invention include those wherein said substituent group is a group of the formula $—COR_3$, wherein $R_3$ is selected from the group consisting of an aliphatic group containing 1 to 12 carbon atoms, more preferably 1 to 8 carbon atoms, most preferably 1 to 4 carbon atoms; an arylaliphatic group containing 1 to 12 carbon atoms, more preferably 1 to 10 carbon atoms, most preferably 1 to 9 carbon atoms; and a heterocyclic group containing 4 to 6 carbon atoms, each of said groups containing a basic nitrogen atom or a quaternary ammonium group. The arylaliphatic group can be an arylalkyl group wherein the aryl group can be a benzene ring, and the alkyl group contains 1 to 3 carbon atoms. The arylaliphatic group can have a basic nitrogen atom or quaternary ammonium group on the aliphatic moiety attached to the ester group of the brefeldin A derivative, or on a side chain of the aryl moiety of the arylaliphatic group.

One of $R_1$ and $R_2$ can be a group of the formula:

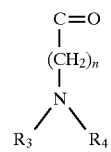

wherein n is an integer of 1 to 3, and $R_3$ and $R_4$ are independently or identically selected from the group consisting of hydrogen and an alkyl group having from 1 to 3 carbon atoms, or wherein $R_3$ and $R_4$ together with the nitrogen atom to which they are attached form a saturated or unsaturated heterocyclic ring having 4 to 6 carbon atoms wherein 1 to 2 of said carbon atoms can optionally be replaced by heteroatoms. These additional heteroatoms can be selected from N, S, and O. If the heterocyclic ring contains only one nitrogen atom, the number of carbon atoms would be 4 to 6. If the heterocyclic ring contains two heteroatoms, one of which is nitrogen, the number of carbon atoms is 3 to 5. A 7 membered heterocyclic ring can contain 2 or 3 heteroatoms, of which one would be nitrogen; with 2 heteroatoms, the number of carbon atoms would be 5, and with 3 heteroatoms, the number of carbon atoms would be 4.

$R_3$ can be a group of the formula $—CH_2N(CH_3)_2$, or a residue obtained by removing the carboxyl group of an amino acid. Said amino acid can be selected from the group consisting of glycine, alanine, leucine, isoleucine, valine, phenylalanine, proline, lysine and arginine.

Said heterocyclic ring having 1 to 2 heteroatoms can be selected from the group consisting of a piperazine ring, a methylpiperazine ring, a morpholine ring, a methylmorpholine ring, a perhydrothiazine ring, a methylperhydrothiazine ring, a pyrazoline ring, an isoxazoline ring, an oxazoline ring, a 1,2-oxazoline ring, a perhydropyridazine ring, a perhydrotriazine ring, a perhydrooxathiazine ring, a perhydrooxadiazine ring, an imidazoline ring, a thiazoline ring, an isothiazoline ring, a 1,2,4-oxadiazoline ring, a 1,2,5-oxadiazoline ring, a 1,2,3-triazole ring, a 1,2,4-triazole ring, an azepine ring, a perhydroazepine ring, a 1,2,4-diazepine ring, a perhydrodiazepine ring, a perhydrooxazepine ring, and a perhydrothiazepine ring.

In the non-limiting examples presented below, one of $R_1$ and $R_2$ is a group of the formula —COCH$_2$N(CH$_3$)$_2$, and the particular compounds are 4-O-(N,N-dimethylglycyl) brefeldin A, or a pharmaceutically acceptable salt thereof, and 7-O-(N,N-dimethylglycyl)brefeldin A, or a pharmaceutically acceptable salt thereof.

As is evident from Formula (II), the compounds of the present invention can be characterized as mono esters, that is, only one of the hydroxyl groups of brefeldin A is esterified.

General procedures available in literature for esterification of secondary hydroxyl groups, such as those present in brefeldin A, do not offer selectivity in producing the mono esters. In general, it is customary to use a huge excess of the reactant to produce the bis-ester (see, for example, Acker et al., U.S. Pat. No. 4,608,078). However, in the present invention, an attempt was made to produce the mixtures with a view toward separating the mono esters by simple manipulations, such as crystallization or chromatography. Thus, when brefeldin A is treated with a representative synthetic amino acid, N,N-dimethylglycine, in the presence of 1,3-dicyclohexylcarbodimide (DCC) and 4-dimethylaminopyridine (DMAP), it produces a mixture of products. From this mixture, it is possible to isolate by chromatographic separation the mono ester, Formula III, functionalized at position 4, in about 15% yield. The mono ester corresponding to the 7-OH group of brefeldin A (Formula IV) could not be isolated from this reaction. A small spot corresponding to the ester IV could be detected by thin layer chromatography, but the reaction was not scaled up to isolate IV since an alternate method was devised to produce this compound in high yield. Nevertheless, this process is useful for obtaining sufficient 4-O-ester.

A different strategy is used for the preparation of the ester represented by Formula IV. To produce this compound, brefeldin A is first converted to the chloroacetate ester using chloroacetyl chloride in presence of a base such as 1,8-diazabicyclo[5.4.0]undec-7-ene (DBU). The resulting chloroacetate ester is then converted to N,N-dimethyl-glycinate ester by treatment with dimethylamine. This two step process results in an excellent yield of the ester represented by Formula IV.

Using the above synthetic strategies, one can prepare brefeldin A mono esters and bis-esters represented by the general Formula II, where $R_1$ or $R_2$ is represented by an alkyl, aryl, arylalkyl, or heterocyclic amine radical, with or without additional substituents. It is also conceivable that the above synthetic strategies may be used to construct molecules in which the $R_1$ or $R_2$ groups represent radicals other than hydrogen, with the stipulation that one of such groups (either $R_1$ or $R_2$) bears a basic nitrogen function such as an amine suitable for conversion to water soluble salts.

Figure 4B:
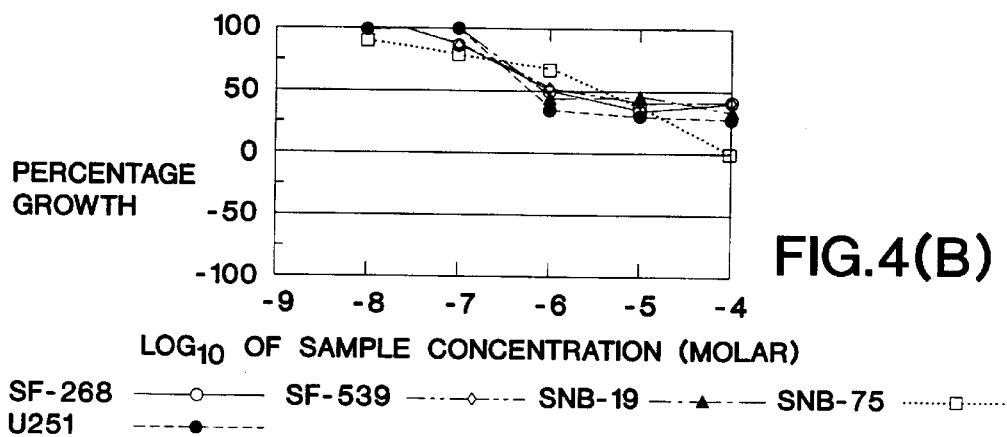
Figure 4C:
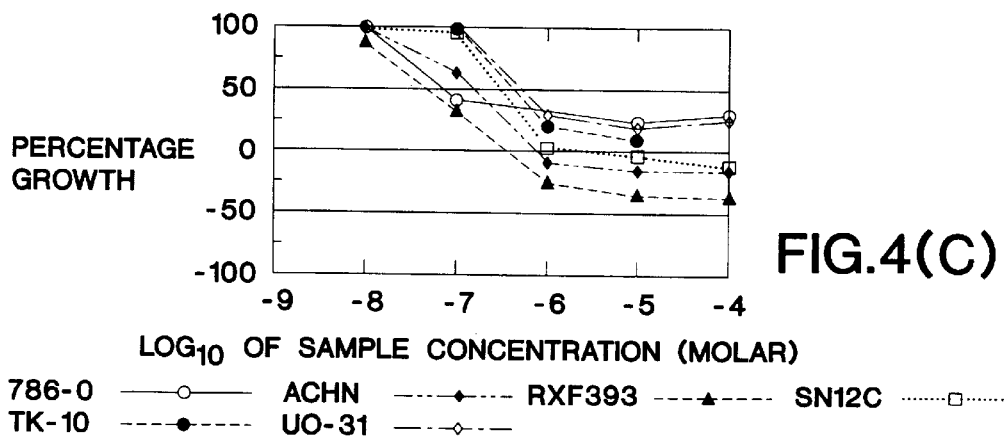
Figure 4D:
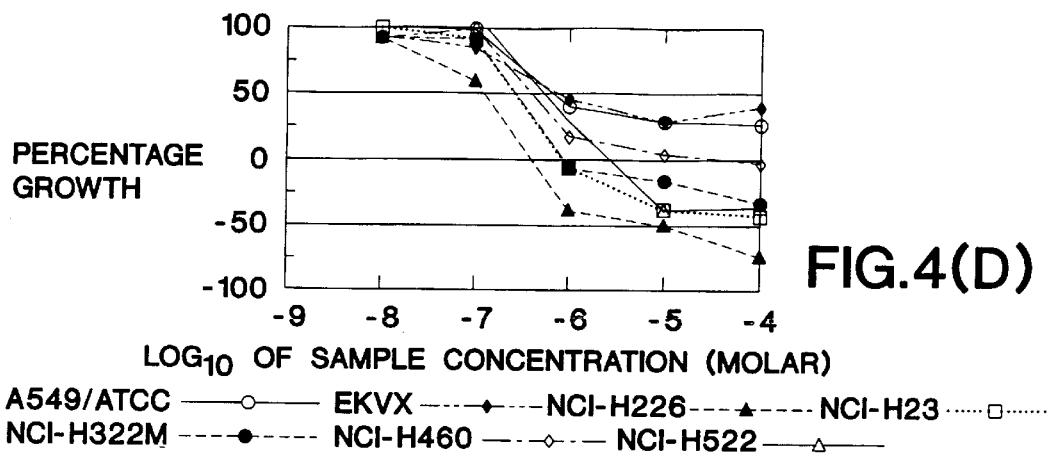
Figure 4E:
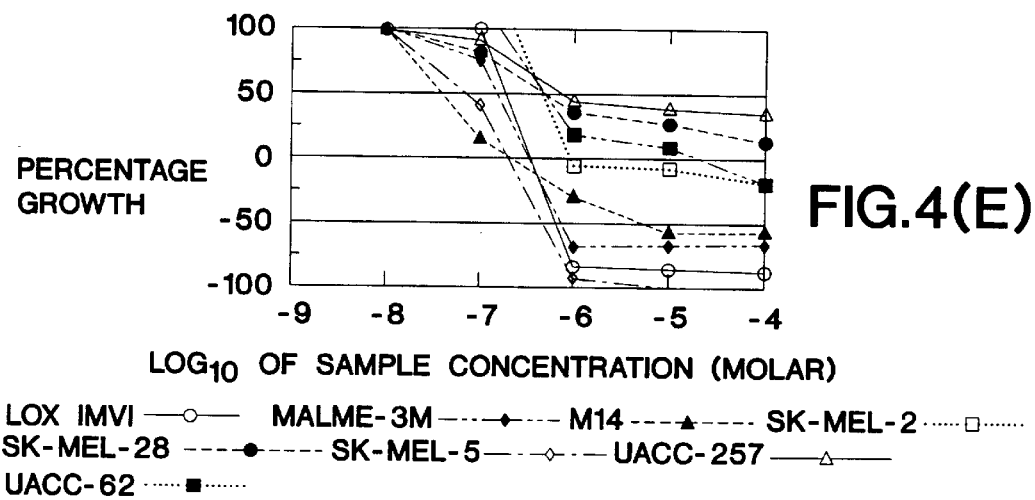
Figure 4F:
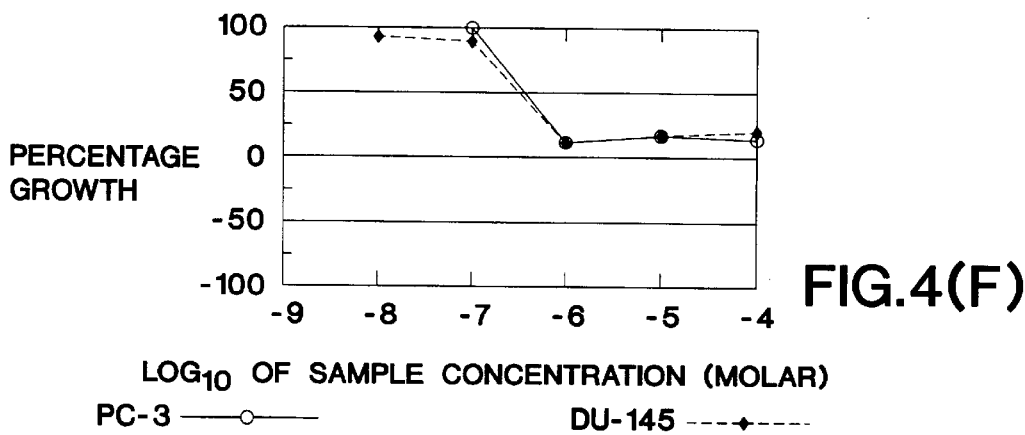
Figure 4G:
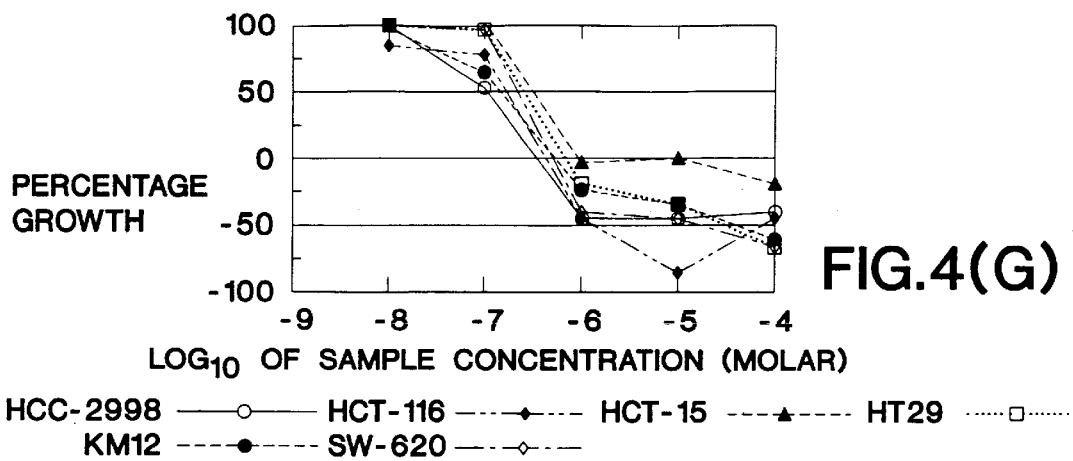
Figure 4H:
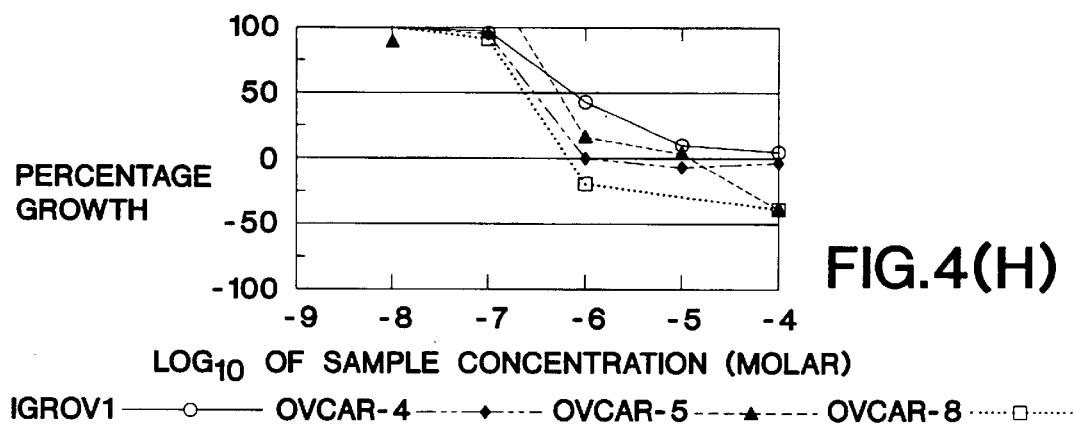
Figure 4I:
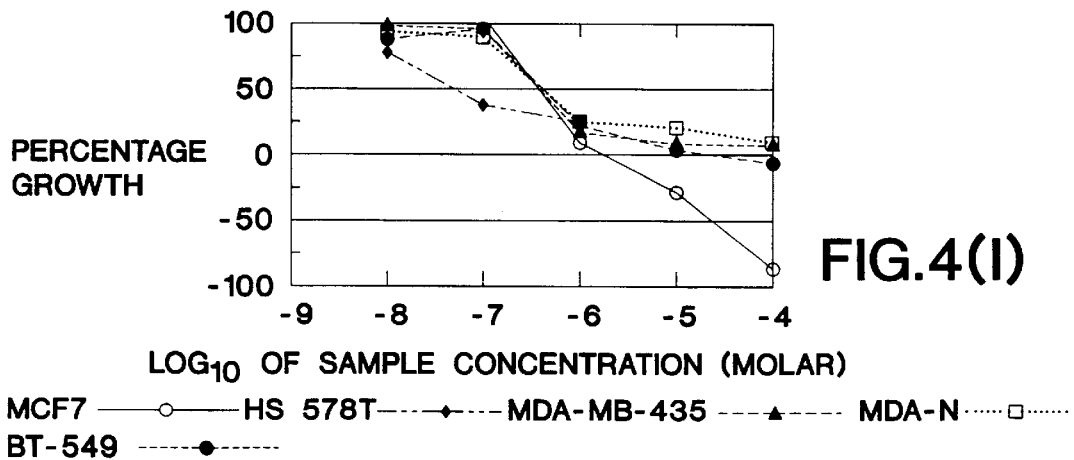
Figure 5A:
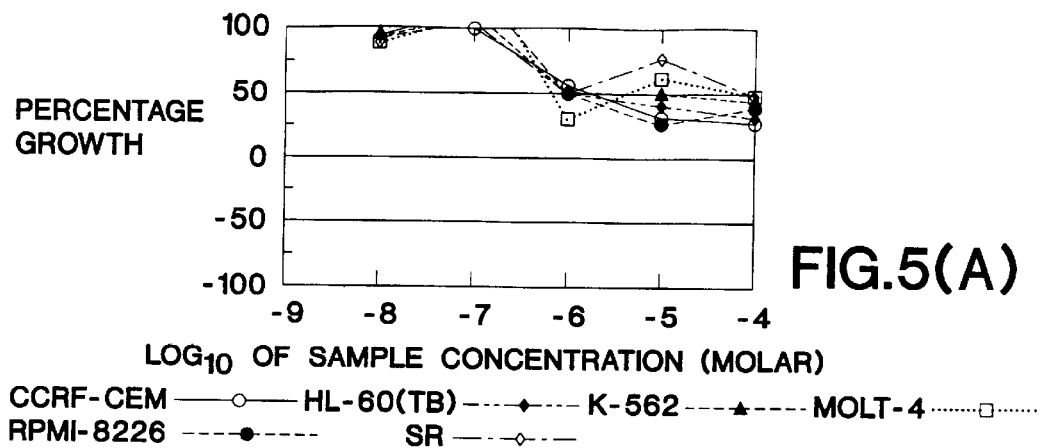
Figure 5B:
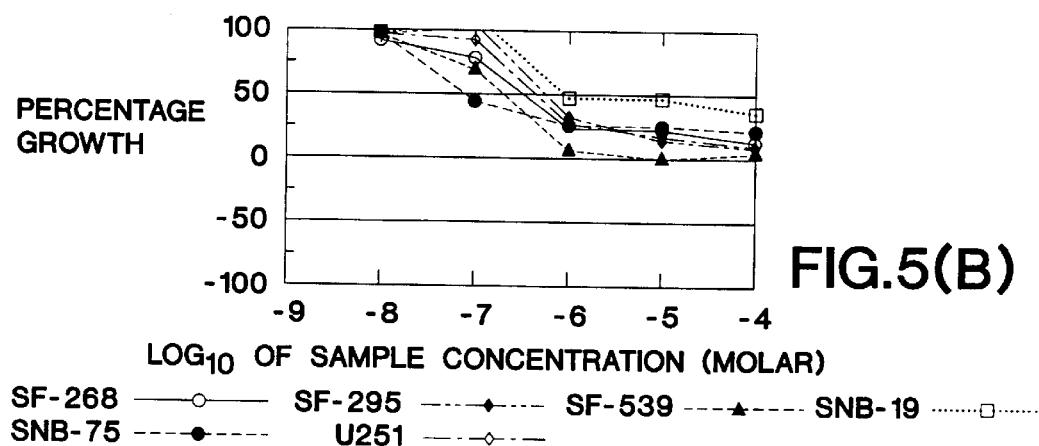
Figure 5C:
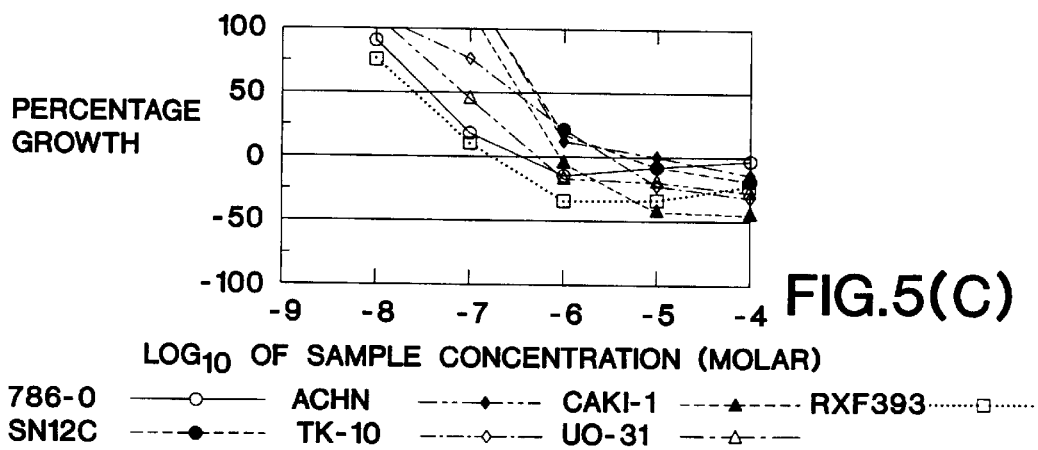
Figure 5D:
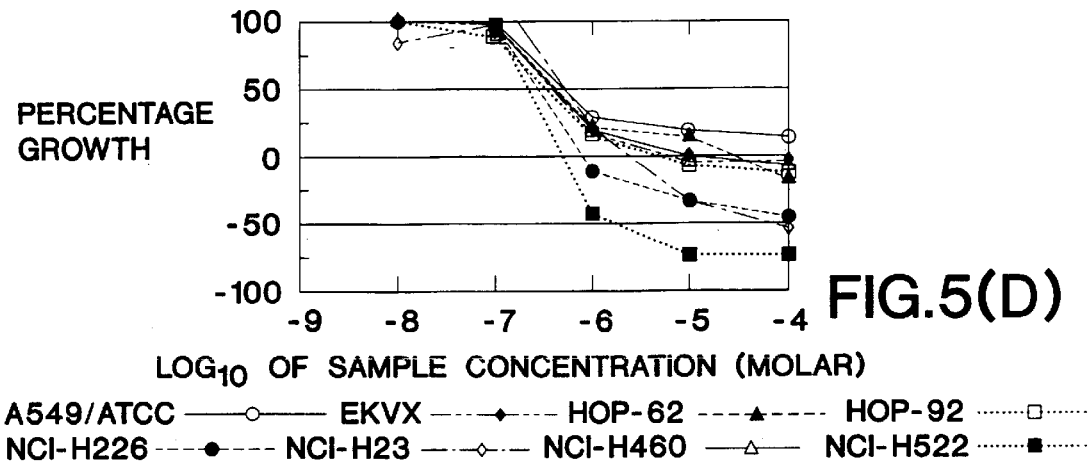
Figure 5E:
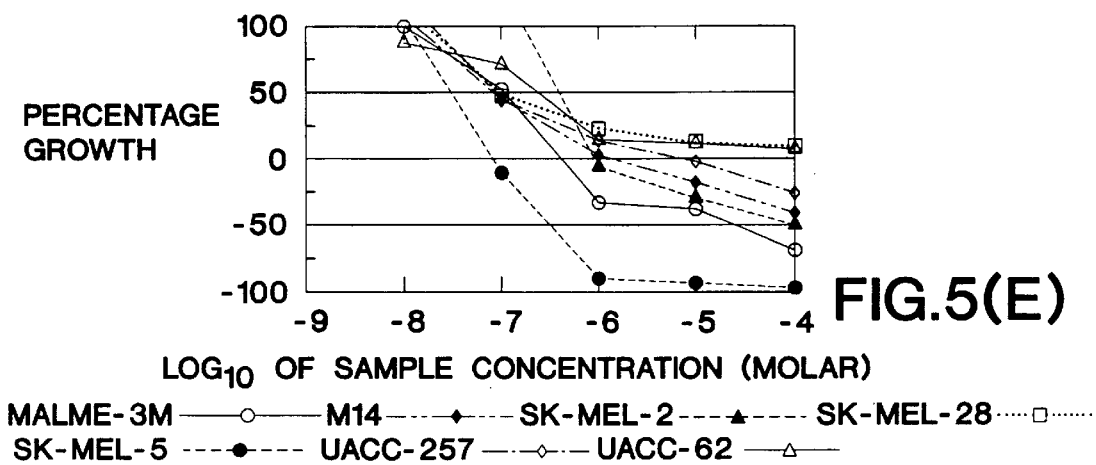
Figure 5F:
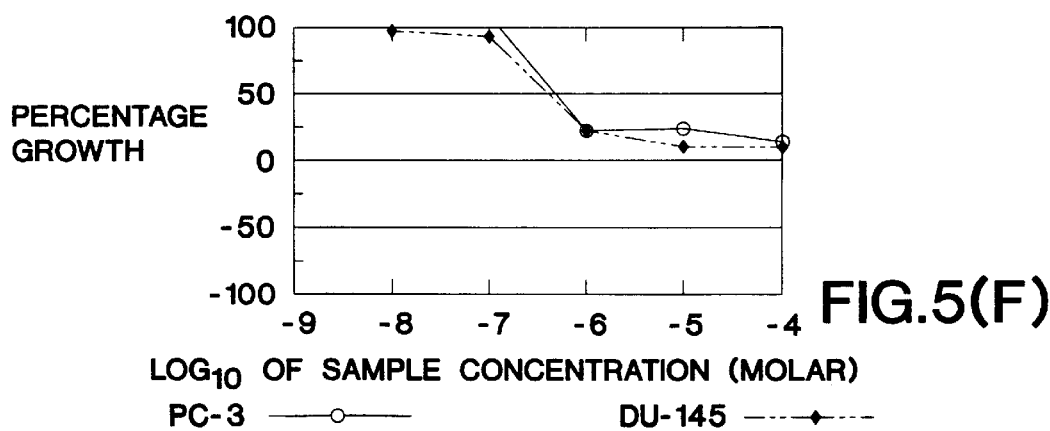
Figure 6A:
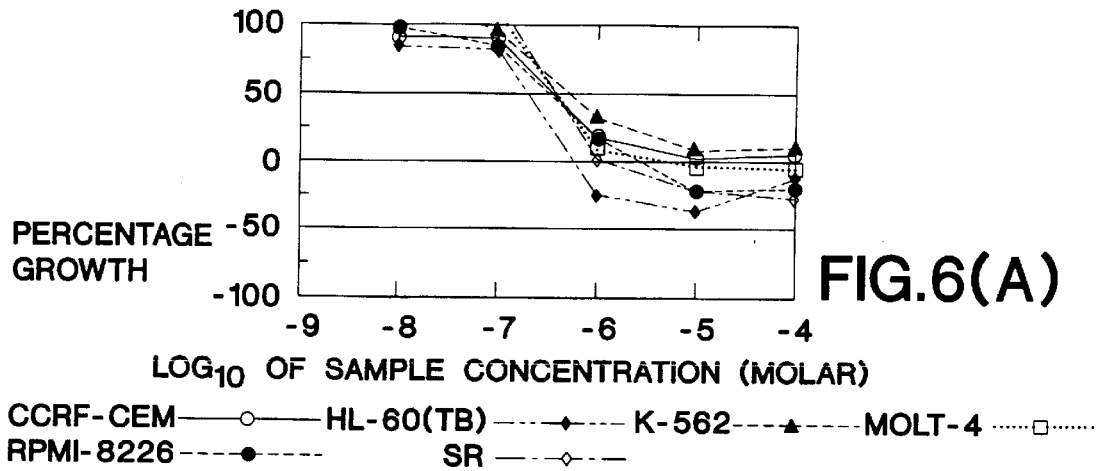
Figure 6B:
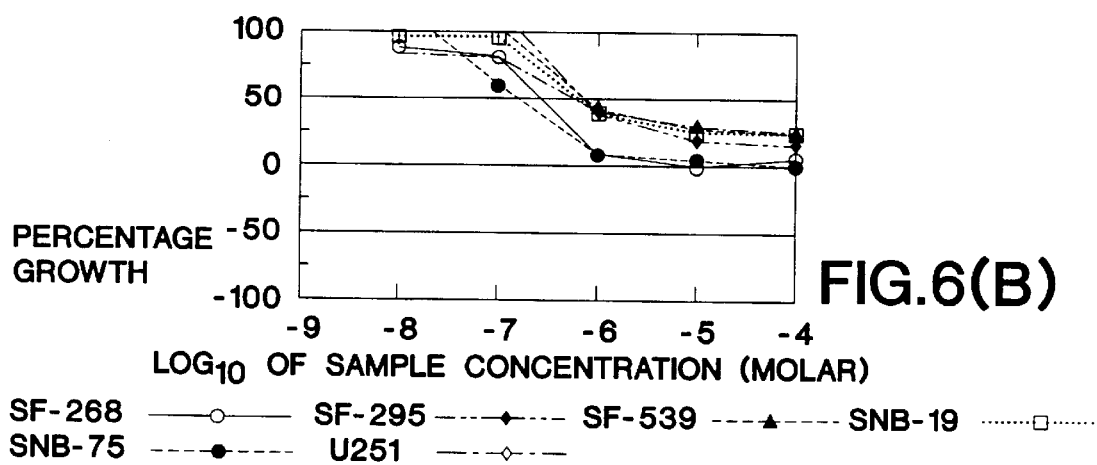
Figure 6C:
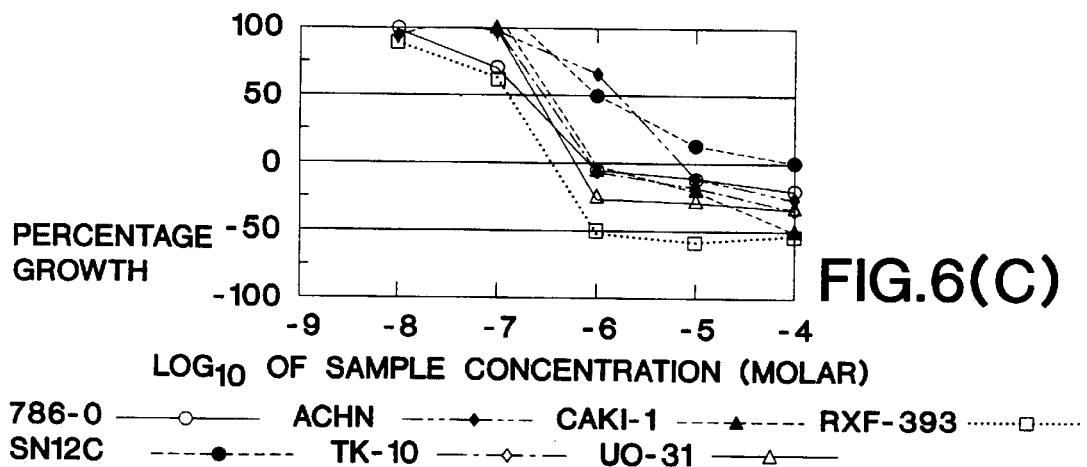
Figure 6G:
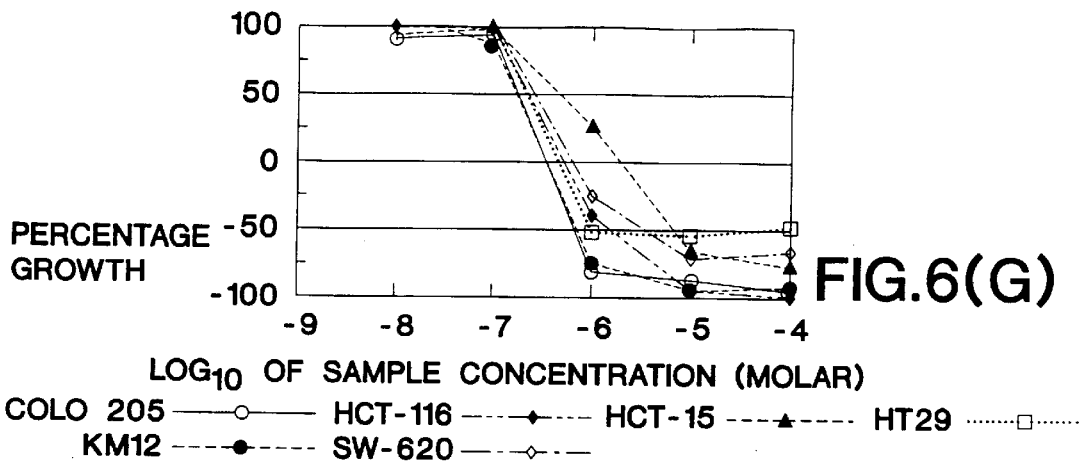
Figure 6H:
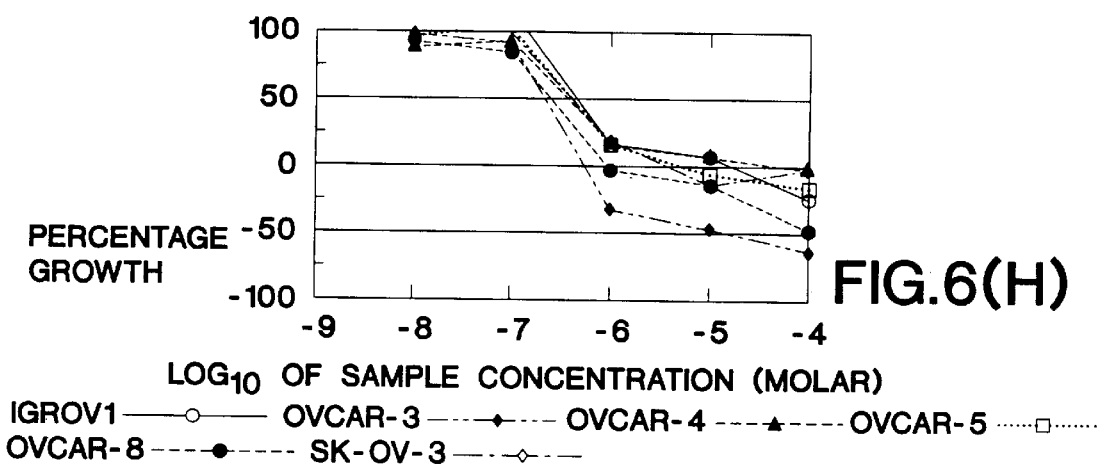
Figure 6I:
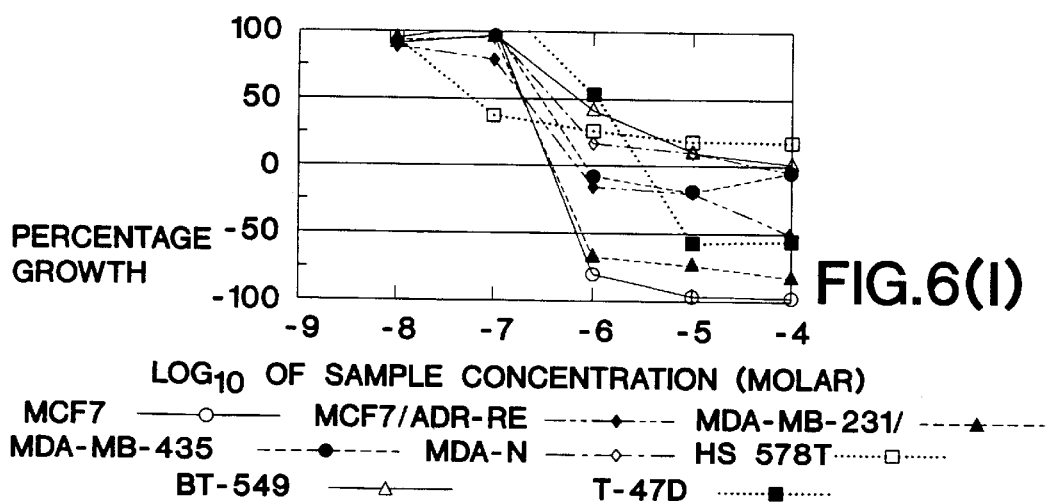

FIGS. 1, 2, and 3 describe the in vitro activities of brefeldin A (Formula I) and its esters III and IV. The dose-response curves for these compounds are provided in FIGS. 4, 5, and 6. It is clear that brefeldin A and the present esters have similar cytostatic and cytocidal activities in human cancer cell lines.

PREPARATIVE PROCEDURES

Example 1

To a stirring suspension of brefeldin A (1.78 m.mol), 4-dimethylaminopyridine (1.45 m.mol), and N,N-dimethylglycine (1.78 m.mol) in dichloromethane (25 ml) at room temperature is added 1,3-dicyclohexylcarbodiimide (DCC, 5.21 m.mol). After stirring for 24 hours, additional DCC (1.74 m.mol) is added, and the stirring continued for an additional 24 hours. The precipitated solid is removed by filtration. The filtrate is concentrated under reduced pressure and the residue dissolved in EtOAc, clarified by filtration, and loaded on a silica gel column previously packed in EtOAc. Elution with EtOAc gives unreacted brefeldin A, and elution with EtOAc:CH$_3$OH (95:5) gives the desired mono ester product, Formula III. The ester compound of Formula IV could be detected by thin layer chromatography as a faint spot, but could not be isolated. Fractions containing the product Formula III are combined and concentrated under vacuum to afford after recrystallization from EtOAc:Hexane pure ester, Formula III, mp 60°–62°. Overall yield is 15%. The NMR, IR, and mass spectrum are compatible with the structure of the product, which is set forth in Formula (III). Elemental Analysis; calculated for $C_{20}H_{31}NO_5$ 0.5 H$_2$O: C, 64.15; H, 8.61; and N 3.74; Found: C, 64.32; H, 8.73; and N 3.78.

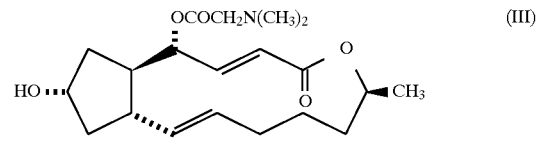

This compound is freely soluble (10–50 mg/ml) in dilute acidic solutions.

Example 2

To a stirred solution of brefeldin A (0.148 mol) and 1,8-diazabicyclo[5.4.0]undec-7-ene (DBU, 0.297 mol) in tetrahydrofuran (THF) (8.2 L) at room temperature, is added a solution of 2.51M chloroacetyl chloride in THF (118.4 ml, 0.297 mol). After heating the mixture at 65° C. over 2 hours, the mixture is cooled to room temperature and the THF solution decanted from the precipitated solid. The solid is washed with THF and combined with the original solution. Anhydrous dimethylamine is bubbled through the solution for 0.5 hour and the mixture stirred for 48 hours at room temperature. The solvent is removed under reduced pressure, and the dark residue is slurried in 200 ml of CH$_2$Cl$_2$ and chromatographed on a silica gel column (2 kg) packed and eluted with EtOAc. Product fractions are combined and concentrated to afford 34 gm of ester IV as a yellow solid. Recrystallization from EtOAc:Hexane afforded pure IV as a white crystalline solid; mp 105°–106° C. The NMR, IR and mass spectrum are compatible with the structure, which is set forth in formula IV. Elemental Analysis; calculated for $C_{20}H_{31}NO_5$; C, 65.73; H, 8.55 and N, 3,83: Found; C, 65.72; H, 8.52 and N, 3.84.

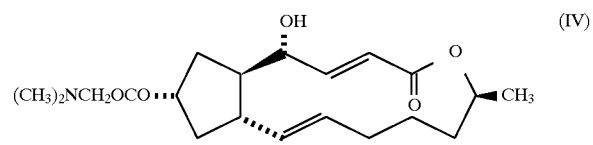

This compound is freely soluble (10–50 mg/ml) in dilute acidic solutions.

Pharmaceutical Preparations

The compounds of the present invention can be formulated per se in pharmaceutical preparations or formulated in the form of pharmaceutically acceptable salts thereof, particularly as nontoxic pharmaceutically acceptable acid addition salts. These salts can be prepared from the compounds of the invention according to conventional chemical methods.

Normally, the salts are prepared by reacting the free base with stoichiometric amounts or with an excess thereof of the desired salt-forming inorganic or organic acid in a suitable solvent or various combination of solvents. As an example, the free base can be dissolved in an aqueous solution of the appropriate acid and the salt recovered by standard techniques, for example, by lyophilization of the solution. Alternatively, the free base can be dissolved in an organic solvent such as a lower alkanol, an ether, an alkyl ester, or mixtures thereof, for example, methanol, ethanol, ether, ethylacetate, an ethylacetate-ether solution, and the like, whereafter it is treated with the appropriate acid to form the corresponding salt. The salt is recovered by standard recovery techniques, for example, by filtration of the desired salt on spontaneous separation from the solution, or it can be precipitated by the addition of a solvent in which the salt is insoluble and recovered therefrom.

The brefeldin A derivatives of the present invention can be utilized in the treatment of cancers including colon cancer, melanoma, leukemia, ovarian, prostate, breast and renal tumors, due to their cytotoxic, antitumor activity. The new compounds can be administered in intravenous dosage form, in which they are formulated into pharmaceutical compositions by combination with appropriate pharmaceutically acceptable carriers or diluents. The new compounds can be used in the form of their pharmaceutically acceptable salts, and also may be used alone or in combination with each other, as well as in combination with other pharmaceutically active compounds. They may be formulated into preparations by dissolving, suspending, or emulsifying them in aqueous or non-aqueous solvents, and if desired, with conventional additives such as solubilizers, isotonic agents, suspending agents, emulsifying agents, stabilizers, and preservatives.

The following Formulation I is an example of an intravenous dosage form comprising a compound of the present invention.

Formulation I

| | |
|---|---|
| Active compound (brefeldin A derivative) | 50 mg |
| Mannitol, USP | 100 mg |
| Hydrochloric acid | (slightly over 1 equivalent) |
| Water for Injection, USP | qs 5 ml |

The foregoing solution is lyophilized to form a white to off-white cake containing amorphous solid, and is stored under refrigeration until use. At the time of use, the vial contents are reconstituted with 5 ml of sterile Water for Injection, USP. Each ml contains 10 mg of the brefeldin A derivative (as HCl salt) and 20 mg of mannitol. The solution exhibits a pH in the range of 2.5 to 4.0.

The compounds of the present invention can be freeze-dried and, if desired, combined with other pharmaceutically acceptable excipients to prepare formulations suitable for parenteral, injectable administration. For such administration, the formulation can be reconstituted in water, normal saline, or 5% dextrose solution, or a mixture of water and an organic solvent, such as propylene glycol, ethanol, and the like.

The dose administered, whether a single dose, multiple dose, or a daily dose, will of course, vary with the particular compound of the invention employed because of the varying potency of the compound, the chosen route of administration, the size of the recipient, and the nature of the patient's condition. The dosage administered is not subject to defined bounds, but will usually be an effective amount, or the equivalent on a molar basis of the pharmacologically active free form produced from a dosage formulation upon the metabolic release of the active drug to achieve its desired pharmacological and physiological effects. The dosage administered is generally in the range of from about 0.8 to about 8 mg/kg of body weight, or about 30–300 mg/m$^2$ of the patient for a treatment course, preferably about 75–250 mg/m$^2$, more preferably about 100–200 mg/m$^2$.

Biological Activity

As noted above, the brefeldin A derivatives of the present invention are useful for their antitumor activity, including activity against colon cancer, melanoma, leukemia, ovarian, prostate, breast and renal tumors.

Evidence of the activity of the present invention compounds is shown in FIGS. 1, 2 and 3, which report the results of in vitro studies on various cell lines utilizing as the test compounds brefeldin A, the compound of Formula III, and the compound of Formula IV, respectively. The dose response curves for the same compounds are shown in FIGS. 4, 5 and 6, respectively.

From these results, it is clear that brefeldin A and the present derivatives exhibit similar cytostatic and cytocidal activity in human cancer cell lines.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for treating tumors, which comprises administering to a patient an effective antitumor amount of at least one compound according to a compound of the formula:

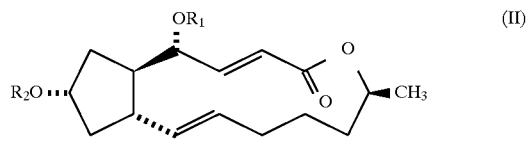

(II)

wherein one of $R_1$ and $R_2$ is H and the other of $R_1$ and $R_2$ is a substituent group having 1 to 12 carbon atoms containing a nitrogen selected from the group consisting of primary amines, secondary amines, tertiary amines, and quaternary ammonium groups and salts thereof.

2. The method according to claim 1, wherein said treatment comprises treating tumors selected from the group consisting of human colon cancer, melanoma, leukemia, ovarian, prostate, breast and renal tumors.

* * * * *